(12) United States Patent
Freer

(10) Patent No.: US 6,402,520 B1
(45) Date of Patent: Jun. 11, 2002

(54) ELECTROENCEPHALOGRAPH BASED BIOFEEDBACK SYSTEM FOR IMPROVING LEARNING SKILLS

(75) Inventor: Peter A. Freer, Asheville, NC (US)

(73) Assignee: Unique Logic and Technology, Inc., Asheville, NC (US)

( * ) Notice: Subject to any disclaimer, the term of this patent is extended or adjusted under 35 U.S.C. 154(b) by 0 days.

(21) Appl. No.: 09/373,419

(22) Filed: Aug. 12, 1999

Related U.S. Application Data

(63) Continuation-in-part of application No. 08/982,774, filed on Dec. 2, 1997, now Pat. No. 6,097,981, which is a continuation-in-part of application No. 08/846,621, filed on Apr. 30, 1997, now abandoned.

(51) Int. Cl.⁷ ............................................... G09B 19/00
(52) U.S. Cl. ...................... 434/236; 434/258; 434/362; 600/544; 600/545
(58) Field of Search .................. 434/236, 258, 434/362; 600/544, 545

(56) References Cited

U.S. PATENT DOCUMENTS

| | | | |
|---|---|---|---|
| 4,140,997 A | | 2/1979 | Brady |
| 4,461,301 A | | 7/1984 | Ochs |
| 4,926,969 A | | 5/1990 | Wright et al. |
| 4,928,704 A | | 5/1990 | Hardt |
| 4,955,388 A | | 9/1990 | Silberstein |
| 5,213,338 A | | 5/1993 | Brotz |
| 5,219,322 A | | 6/1993 | Weathers |
| 5,279,305 A | | 1/1994 | Zimmerman et al. |
| 5,343,871 A | | 9/1994 | Bittman et al. |
| 5,377,100 A | * | 12/1994 | Pope et al. .................. 600/545 |
| 5,447,166 A | | 9/1995 | Gevins |
| 5,540,235 A | | 7/1996 | Wilson |
| 5,571,057 A | | 11/1996 | Ayers |
| 5,724,987 A | * | 3/1998 | Gevins et al. .......... 600/544 X |
| 5,740,812 A | | 4/1998 | Cowan |
| 5,746,205 A | * | 5/1998 | Virsu et al. ............. 600/544 X |
| 5,755,230 A | | 5/1998 | Schmidt et al. ............. 600/545 |
| 5,899,867 A | | 5/1999 | Collura |
| 5,911,581 A | * | 6/1999 | Reynolds et al. ........ 434/236 X |
| 6,053,739 A | * | 4/2000 | Stewart et al. .......... 434/236 X |
| 6,097,927 A | * | 8/2000 | LaDue .................... 434/308 X |
| 6,099,319 A | * | 8/2000 | Zaltman et al. ......... 434/236 X |
| 6,156,014 A | * | 12/2000 | Jenkins et al. .......... 434/169 X |

* cited by examiner

*Primary Examiner*—John Edmund Rovnak
*Assistant Examiner*—Chanda Harris
(74) *Attorney, Agent, or Firm*—Carter & Schnedler, P.A.

(57) ABSTRACT

Apparatus utilizing electrical activity of the brain to control a series of low-stimuli educational exercises displayed on a computer monitor to increase the following. educational components: time on-task, visual tracking, short-term memory, visual discriminatory processing, auditory discriminatory processing, and focus. The exercises are governed by real-time analysis of the focus and processing states of the user. Specific relative exercise performance data are collected and recorded from the use of each of the educational components to demonstrate improvement over time of the user in each of the sited educational components.

52 Claims, 29 Drawing Sheets

ELECTROENCEPHALOGRAPH BASED BIOFEEDBACK SYSTEM FOR IMPROVING LEARNING SKILLS

CROSS-REFERENCE TO RELATED APPLICATIONS

This is a continuation-in-part of Patent No. 6,097,981, filed Dec. 2, 1997, now U.S. Pat. No. 6,097,981 which is in turn a continuation-in-part of application Ser. No. 08/846,621, filed Apr. 30, 1997, now abandoned, the entire disclosures of which are hereby expressly incorporated by reference.

BACKGROUND OF THE INVENTION

The present invention relates generally to biofeedback systems and, more particularly, to apparatus incorporating electroencephalograph (EEG) based biofeedback method for improving attention (which may also be referred to as focus) and learning skills of a user.

The ability to concentrate or pay enough attention to information allows the brain to transfer the information to short-term memory and then encode some of that information into long-term memory. Paying enough attention is the key.

According to the Minimal Stimulus Theory (MST.), the attention of an individual is dependent upon certain thresholds of stimuli entering the brain to cause arousal or initiation of the process of attention. Some individuals require more stimulation than others. As used herein, the term "stimulation" is meant to include the elements of attention arousal including interest, motivation, and significance. If there is not enough stimulation, then attention is not aroused.

The capacity for sustained attention usually improves throughout childhood and early adolescence. The improvement in attention is due largely to the maturational changes in the central nervous system. The area of the brain responsible for the regulation of attention, i.e. the reticular formation, is not fully developed or myelinated until puberty. Myelination is the process by which neurons are encased in waxy myelin sheaths that facilitate transmission of neural impulses.

Trauma, lack of stimuli, disease, chemical imbalances, and various other factors affect the capacity of the brain to fully attend to tasks.

The present invention offers the user the opportunity to practice attention growth while simultaneously attending to those factors which comprise perception and which thus affect attention. Furthermore, the present invention may be implemented according to one or more educational cognitive psychology theories, especially those which focus on the development of attention or concentration.

Information processing begins with the perception of information, i.e. a stimulus. The information is accepted and held for a very brief period in a sensory memory store. Although the capacity of sensory memory appears to be unlimited, the mode of representation is sensory and thus the duration is very brief. For example, visual information may last approximately one half second in sensory memory. Loss then occurs according to a time rate of decay.

The area of primary importance in the learning of new information begins when an individual selectively pays attention to the incoming stimulus before perception of the stimulus decays. Attention is selective. At any given moment, attention is focused on only a minute portion of the stimulation impinging on sensory receptors. During periods of focus, a person tries to concentrate attention on an object or event while ignoring irrelevant or distracting sensations. If a person is able to pay enough attention to the stimulus before it decays, some of the information may be transferred to short-term memory (STM). STM can be considered to be active consciousness or awareness. The capacity of STM appears to be quite limited. For example, a person may be able to think about only five things at one time. Thus, information input may be viewed as a modification of the sensory input and is therefore short in duration. Typically, items are lost after eighteen seconds unless there is active rehearsal. Moreover, loss may occur due to the introduction of new items in STM. A portion of the STM may be referred to as working memory which can be used to perform mental calculations.

Information may be encoded to long-term memory (LTM) if continued attention is paid to the information in the STM by means .of rehearsal. Some of that information may be retained permanently. The LTM apparently has unlimited capacity and can retain information for long periods of time. Information may not effectively be encoded into the LTM when other competing information, or attention thereto, interferes with or taxes the rehearsal process. Information may also be lost from the LTM when other information interferes with retrieving the target information.

The present invention uses an educational protocol which incorporates hierarchical mastery of skills, including visual discrimination, auditory discrimination, and/or increased sensory perception.

SUMMARY OF THE INVENTION

Exemplary embodiments of the invention combine educational protocols with the monitoring of brainwave activity to educate the user about his attentive state. Various protocols are implemented as educational exercises on a video display in the guise of a video game to increase user interest, which incorporate feedback based on levels of attentive state and cognitive processing. Educational skills developed include attention, visual tracking, time on-task, short-term memory data-sequencing, visual-discriminating processing, and auditory discriminating processing.

BRIEF DESCRIPTION OF THE DRAWINGS

While the novel features-of the invention are set forth with particularly in the appended claims, the invention, both as to organization and content, will be better-understood and appreciated, from the following detailed description taken in conjunction with the drawing, in which:

DETAILED DESCRIPTION

Figure 1:
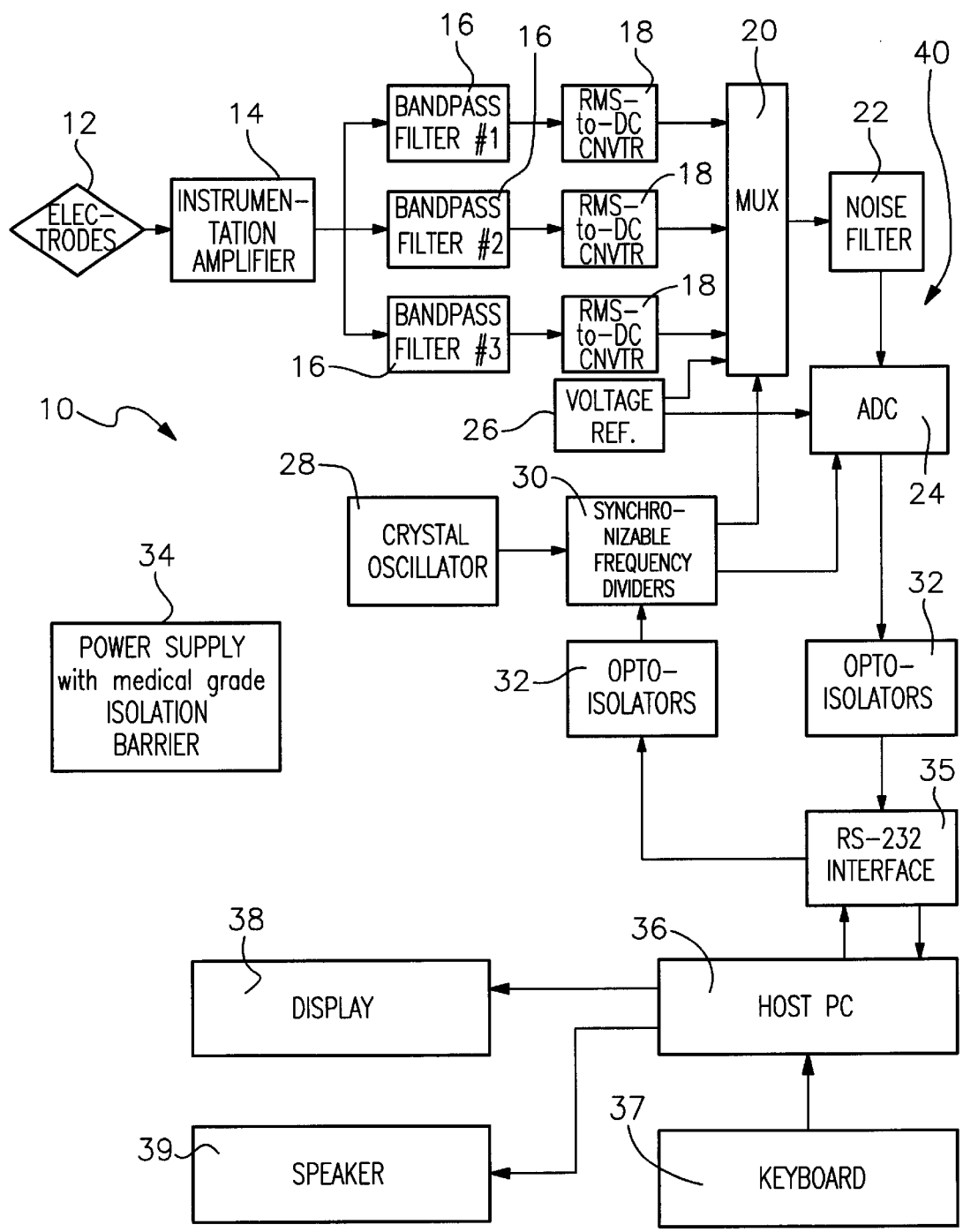
FIG. 1 is a schematic block diagram of one embodiment of an EEG based biofeedback system according to the present invention.

Referring first to FIG. 1, shown is a schematic block diagram of am exemplary apparatus 10 embodying the invention, in the general form of an EEG based biofeedback system 10. The block diagram of FIG. 1 implies the implementation of various functions in hardware. However, as a matter of design choice it will be appreciated that there are a number of functions, such as bandpass filtering and threshold detection, that can as well be performed in software.

The EEG based biofeedback system 10 comprises electrodes 12, an instrumentation amplifier 14, bandpass filters 16, RMS-to-DC converters 18, an analog multiplexer 20, noise filtering 22, an analog-to-digital converter (ADC) 24, a voltage reference 26, a crystal oscillator 28, synchronizable frequency dividers 30, opto-isolators 32, a power supply 34, an RS-232 serial data interface 35, and a host personal computer (PC) 36. Connected to the computer 36 are an input device in the form of a keyboard 37, and a visual output device in the form of a display 38, and an audible output device in the form of a speaker 39.

The electrodes 12, which are placed on the head of a user, are used to pick up the very low level (microvolts) EEG signals. For example, theta waves have amplitudes in the range of 1 to 100 microvolts, while beta waves have amplitudes in the range of 1 to 4 microvolts. These signals are then conveyed via cables to the instrumentation amplifier 14. The instrumentation amplifier 14 is a low level, low noise, floating, differential input, high common mode rejection amplifier. The instrumentation amplifier 14 performs the function of extracting the very weak EEG signals from a typical noisy environment.

The bandpass filters 16 separate the various bands of brain wave activity. This function is performed by analog filters as shown in FIG. 1, but filtering may as well be performed in software. Two frequency bands are particularly relevant in exemplary embodiments of the invention, although others may be employed. An increased level of theta wave activity (approximately 4 Hz to 7 Hz) indicates a lapse of attention. Thus a decrease in theta wave activity indicates increased focus or attention. An increased level of beta wave activity (approximately 12 Hz to 16 Hz) indicates increased cognitive processing.

The RMS-to-DC converters 18 detect the magnitude of brain wave activity within each band of interest. The detected signals are used to reduce the bandwidth of data that must be digitized and sent to the host PC 36. The analog multiplexer (MUX) 20 is an electronic switch used as a data selector to present to the ADC 24 only the data channel that has been selected for analog to digital conversion. The noise filtering 22 is used to remove both random noise and spikes that are generated by other electronic switching circuits within the system. The ADC 24 is used to convert the analog signal (selected by the MUX 20) into a digital (or numerical) value. As a matter of convenience, the ADC 24 used here provides a serial data output stream for each conversion made. The voltage reference 26 is needed for the ADC to convert unknown signal levels into calibrated DC voltages. The voltage reference 26 is also injected as one of the MUX 20 input channels so that the software running on the host PC 36 can verify proper operation of the circuitry.

The crystal oscillator 28 provides a time base. This time base serves several necessary functions. First, it is the "clock" frequency used by the ADC 24 to perform its conversions. Second, the particular frequency chosen provides, through a simple integer division ratio, one of the standard RS-232 baud rates for the serial data communications through the RS-232 serial data interface 35. Third, the master crystal oscillator frequency is divided down by a variety of different integers to set the programmable filters which comprise the bandpass filter set 16. Lastly, a pair of reset table dividers provide a synchronizable low frequency that is used to trigger the ADC 24.

The synchronizable frequency dividers 30 are used not only to trigger the ADC 24 as mentioned above, but also to synchronize software commands to ensure that the data to the host PC 36 maintains an integral relationship to the frame rate of an associated video monitor. This is useful in providing flicker free performance of an animation on the display 38 while simultaneously collecting and analyzing the digitized brain wave data in real time. This type of divider circuit provides a constant frequency output that is just slightly. altered to bring it into synchronization with a synchronizing pulse, which in this case is sent by the host PC 36.

The opto-isolators 32 are used to provide a very high degree of electrical isolation between the user (with electrodes connected) and the computer system.

The power supply 34 is needed for the main electronic circuits. Preferably, a power supply having a high isolation barrier is maintained between the user and the AC power line which is connected to the power supply 34.

The RS-232 serial data interface 35 provides for the serial data communications between the host PC 36 and the other circuitry. Before the isolated serial data can be transferred to and from the host PC 36, the signal levels must be changed to the standard RS-232 signal levels (from the typical 5 volt logic levels).

The host PC 36 provides two functions. First, it runs the display 38 and the user interface that provides the feedback to the user. Second, it performs the inter-related functions of data collection and analysis. Without this second function (which preferably-occurs in the background), there would be no control of the display 38 related to the user's brain wave activity.

Typically, all of the above-described components except for the host PC 36 are preferably contained in a separate hardware unit, designated hereinafter by numeral 40.

During operation of the exemplary embodiment, the hardware unit 40 sends a two byte number specifying a voltage approximately every 67 msecs over the RS-232 line to the host PC 36. The arrival of each byte triggers a very brief, custom interrupt routine in the host PC 36. The interrupt routine determines whether the byte is the first or the second byte in the pair by checking a parity bit, and puts the data in the proper buffer memory location. It has been determined that this rate of RS-232 interrupts does not interfere with the animation.

The host PC 36, meanwhile, follows a cycle of selecting the brain wave to be sampled, reading the data, and using the data. This cycle is important to keep the animation smooth by never trying to do too much at once during the cycle. Each step in the cycle lasts one video frame, the time between one video blanking signal and the next. The duration between video blanks is 1/60 sec, about 66.67 msec. The video blanking signal is on when the electron beam in a cathode ray tube (CRT) monitor 38 moves from the bottom right corner of the screen to the top left in order to begin painting the next video frame's image.

The entire cycle may comprise N steps or timing increments. In the first step, the host PC 36 sends a message to the separate hardware unit 40 or box which indicates which brain wave band is selected for data transmissions. Four such channels may be available: a reference voltage, a theta band, an alpha band, and a beta band. In the Nth step, the host PC 36 reads the-data buffer memory and retrieves the last data placed there by the interrupt routine. It has been determined empirically that different host processor speeds require waiting a different number N' of video frames after triggering a new channel in order to let the electronics in the separate hardware unit 40 settle on the new channel and produce highly stable data. Finally, in the second step of the following cycle, the data is used.

Thus, the interface interactions between the host PC 36 and the separate hardware unit 40 are synchronized to the video animation steps, and dispersed over a standard cycle into the first, second, and Nth steps or time increments. As a result, excessive activity during any one video frame is prevented. If too much activity is attempted during a video frame, then the next video image is not painted and presented soon enough (i.e., the next video frame is not sufficiently displayed), and the eye sees an irregularity in the motion. Typically, much of-the activity of the host PC 36 during each video frame is dedicated toward updating the ongoing animation.

Figure 2:
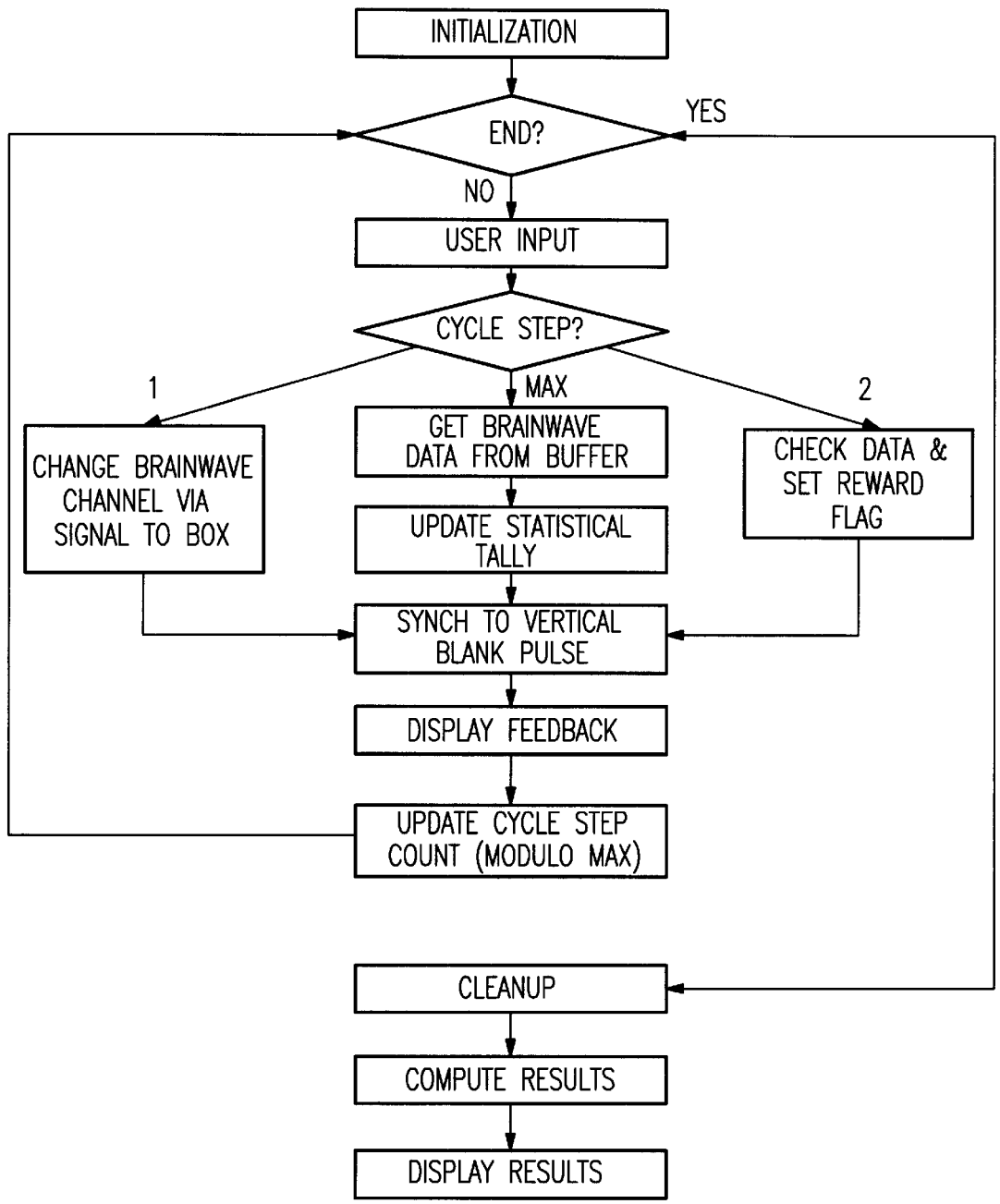
FIG. 2 is a flowchart diagram detailing the logic synchronizing the interface of a host computer to an external hardware unit in an EEG based biofeedback system according to the present invention.

FIG. 2 is a flowchart diagram detailing the logic synchronizing the interface of the host PC 36 to the separate hardware unit 40. Three different tasks in interfacing with the separate hardware unit 40 are spread across several display cycles to avoid a jerky appearance in the animation. An interrupt handling routine places the brain wave data in the buffer for later retrieval. Data arrives from the box at some time between the first and the last (max) cycle step in the total cycle. The total cycle lasts "max" vertical blank cycles of the video display of the host PC 36.

One example of an animation that may be produced in connection with the present invention is that of an image of a bird flying across the video screen. When the user begins to lose attention, as determined from an analysis of one or more user EEG signals, the altitude of the bird begins to decrease. On the other hand, when the user is responding to the stimulus or stimuli (such as the video image) or when the user is fully attentive, the altitude of the bird either increases or is maintained at a constant level, respectively.

Brain wave activity of the user may be measured by detecting the energy levels corresponding to the alpha, beta; and theta frequency bands, having approximate ranges of 8–12 Hz, 12–16 Hz, and 4–7 Hz, respectively. Theta and Beta wave activity may be used as a direct indication of the levels of attention (focus) and cognitive processing of the user. A decrease in theta wave activity indicates increased focus or attention, and an increase in beta wave activity indicates increased cognitive processing.

Figure 3:
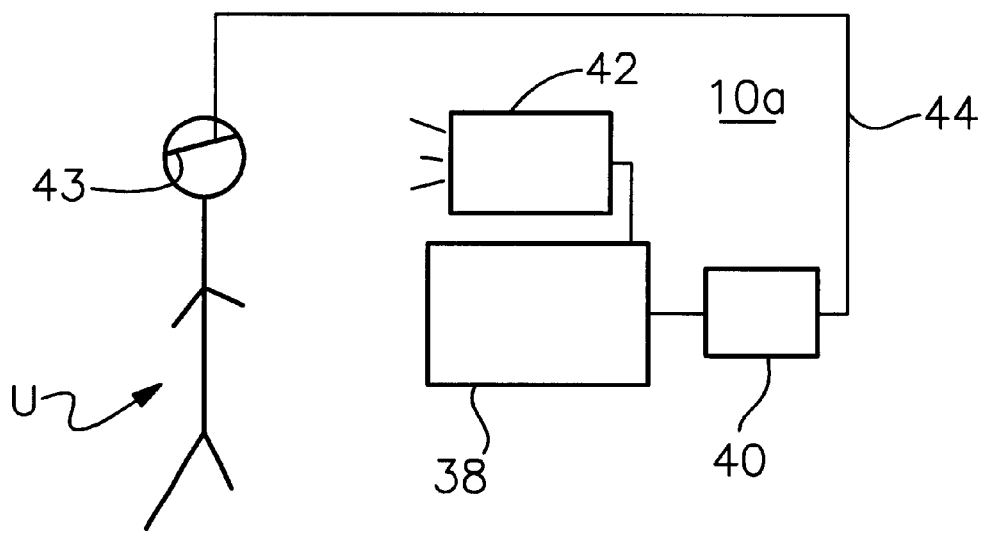
FIG. 3 is a schematic illustration of one embodiment of the present invention wherein a user uses an EEG based biofeedback system to gain proficiency in focusing and controlling attention by manipulating graphical characters on a video screen using the mind alone.

As schematically illustrated in FIG. 3, one embodiment 10a allows a user U to rapidly gain proficiency in focusing and controlling attention by manipulating graphical characters on a video screen 42 using his or her mind alone. The user U dons one or more electrodes, which may be optionally mounted on a headpiece 43, which are connected to hardware unit 40 by connection line 44, and the hardware unit 40 is connected to the host PC 36 which drives a peripheral such as a video screen 42 or audio speaker.

According to one theory, embodiments of the invention are capable of teaching mastery of attention by the stimulation or activation of a natural neural system which may have heretofore been dormant.

The user U can learn to directly control and manipulate action on a computer video screen 42 solely or totally by using his or her attention. This self-learning process may trigger unutilized or under utilized neural pathways or may further trigger the formation of new neural networks and schema. Thus, the user may actually learn how to pay increasing attention to lower and lower levels of stimulation while developing an increased physio-mental capacity for such tasks.

Thus, the present invention EEG based biofeedback system 10a may utilize only the mind of a user to control the computer display. The computer keyboard or other physical control means are required only when turning the computer on or off.

Figure 4:
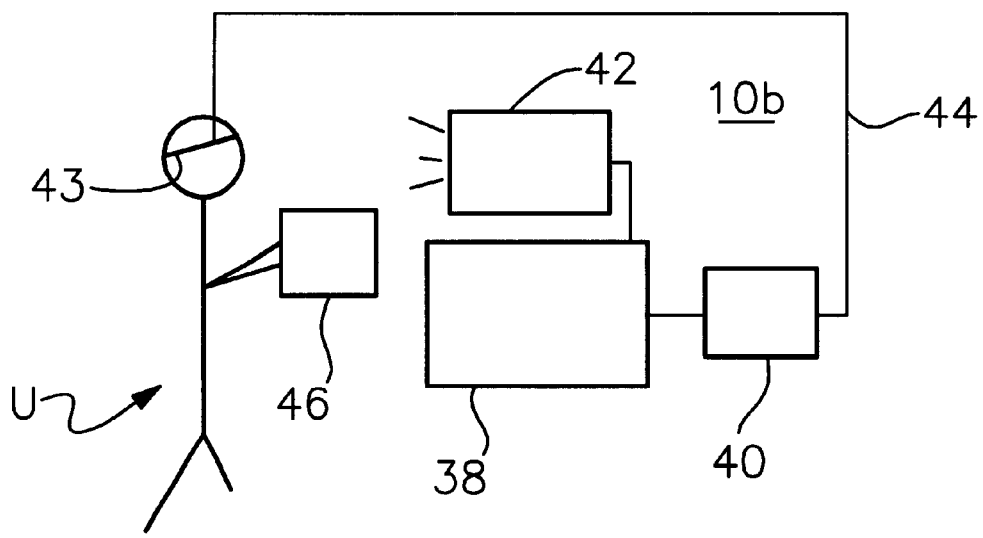
FIG. 4 is a schematic illustration of another embodiment of the present invention, similar to the embodiment shown in FIG. 3, further comprising other modes of input or physical control means.

In another embodiment 10b, as schematically represented in FIG. 4, other modes of input or physical control means or active user input 46. are utilized, such as a computer keyboard or joystick, in conjunction with EEG signals in providing the user U with feedback and/or in controlling and manipulating action on a video screen 42.

In yet another embodiment, an EEG based biofeedback system comprises a probe head piece which does not rely on a physical connection line between the user and another piece of equipment. The headpiece is untethered with respect to other system components. In a particular embodiment, the system includes a probe head piece having one or more EEG electrodes, and an infrared transmission unit connected to the electrodes.

Figure 5:
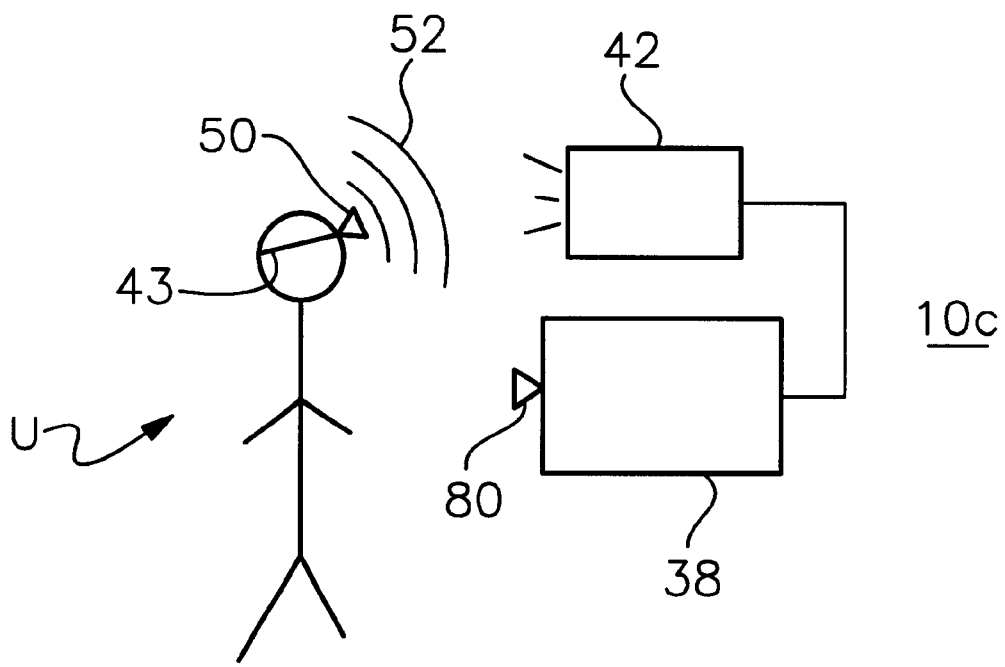
FIG. 5 schematically illustrates another embodiment of the present invention wherein a user wears a headpiece containing EEG probes and an infrared transmitter to gain proficiency in focusing and controlling attention by manipulating a video screen using the mind alone.

FIG. 5 schematically illustrates such an embodiment 10c wherein the user U dons a headpiece 43 containing EEG probes and an infrared transmitter 50 having a battery source and a microprocessor. The headpiece 43 transmits signals corresponding to the EEG readings, via infrared radiation, as denoted by the lines and reference numeral 52.

Figure 6:
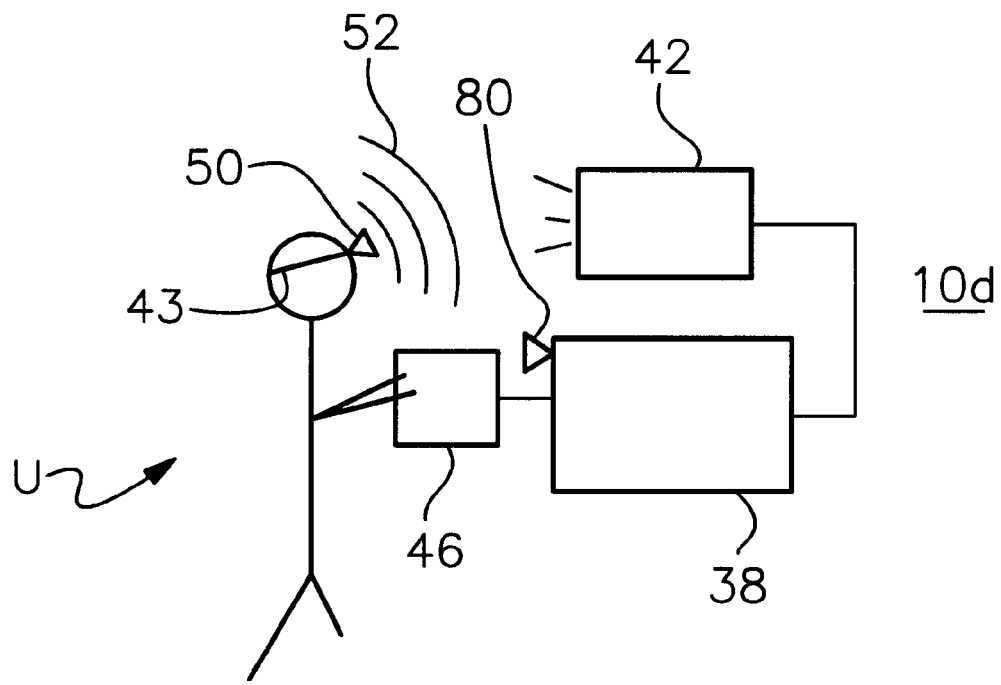
FIG. 6 schematically illustrates yet another embodiment of the present invention, similar to that of FIG. 5, further comprising other modes of input of physical control means.

FIG. 6 schematically illustrates an embodiment 10d similar to that represented in FIG. 5, and further including other active user inputs 46, such as a keyboard, joystick, or pedal.

Figure 7:
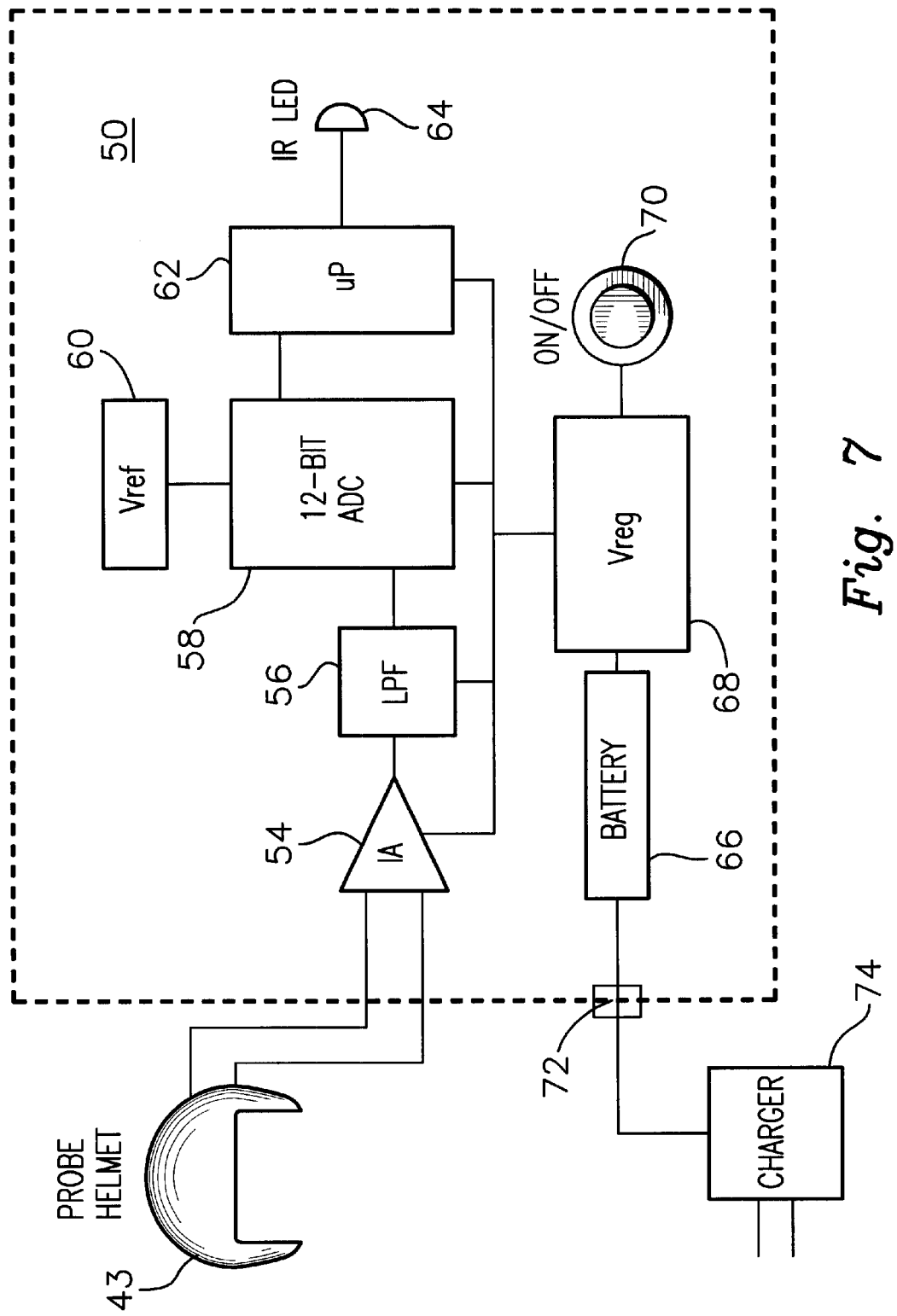
FIG. 7 illustrates an infrared transmitter unit according to the present invention.

FIG. 7 illustrates an embodiment of an infrared transmitter unit 50. The probe head piece 43 is preferably provided with at least three electrodes. At least one of the electrodes is connected to an inverting amplifier 54 which boosts the normally weak EEG signals to improve detection and/or readability. The output of the inverting amplifier 54 passes through a low pass filter 56 and is connected to a 12-bit A/D converter 58. A reference voltage, Vref 60, is input into the A/D converter 58. At least one other electrode serves as a ground, which is not shown in FIG. 7. Output of the A/D converter 58 is directed to a microprocessor 62 which drives an infrared LED 64 which transmits infrared signals. The unit 50 is further provided with a battery 66 whose output is passed through a voltage regulator 68 which supplies power to the inverting amplifier 54, the low pass filter 56, the A/D converter 58 and the microprocessor 62. An on/off switch 70 is provided to control the flow of electrical power from the battery 66 to the various components of the unit 50. Preferably, the battery 66 is provided with a recharging connection 72, and a battery charger 74 may be connected thereto in order to replenish the battery 66. For example, the charger 74 may convert utility line AC current to a suitable DC recharge supply. Preferably, the battery charger 74 may be disconnected from the remaining circuitry. The low pass filter 56 may be a switched capacitor. The A/D converter 58 may be a 12-bit serial multi channel converter. The microprocessor 62 may be a PIC 12C508 micro controller, which may be used to hold the parts count of the unit to a minimum. The unit 50 may operate at approximately 5 volts with a single supply, Vreg 68. The microprocessor 62 may also include control logic or control circuitry to automatically shut off power from the battery 66, for example after a certain time period has elapsed. The microprocessor 62 is preferably adapted to perform the function of separating the various bands of brain wave activity by a digital technique such as Fast Fourier Transforms (FFT). The filtering must be precise and selective. All of the components of FIG. 7, including the microprocessor 62, are mounted in or on the headpiece 43.

By way of a particular example, one primary electrode which is disposed at either the FP1 (right side) or Sensory Motor Rhythm EEG locations is connected to the inverting amplifier 54, a reference voltage electrode is disposed at the right mastoid area, and a ground electrode is disposed at the left mastoid area.

Conversely, in another particular example, one primary electrode is disposed at FP2 (left side) or Sensory Motor Rhythm locations and is connected to the inverting amplifier 54, while the reference electrode is disposed at the left mastoid area, and the ground electrode is disposed at the right mastoid area.

The headpiece 43 may further include a switch which enables the user or the tester to select which electrodes will serve as primary, reference or ground. That is, the headpiece 43 may be provided with a plurality of electrodes connected to a switching means which allow selection of one or more of the electrodes to be electrically connected to a desired component in the headpiece.

Furthermore, the headpiece 43 may comprise a plurality of inverting amplifier 5 and low pass filter circuits (54, 56) to the A/D converter 58 to accommodate more than one primary signal from the electrodes.

Figure 8:
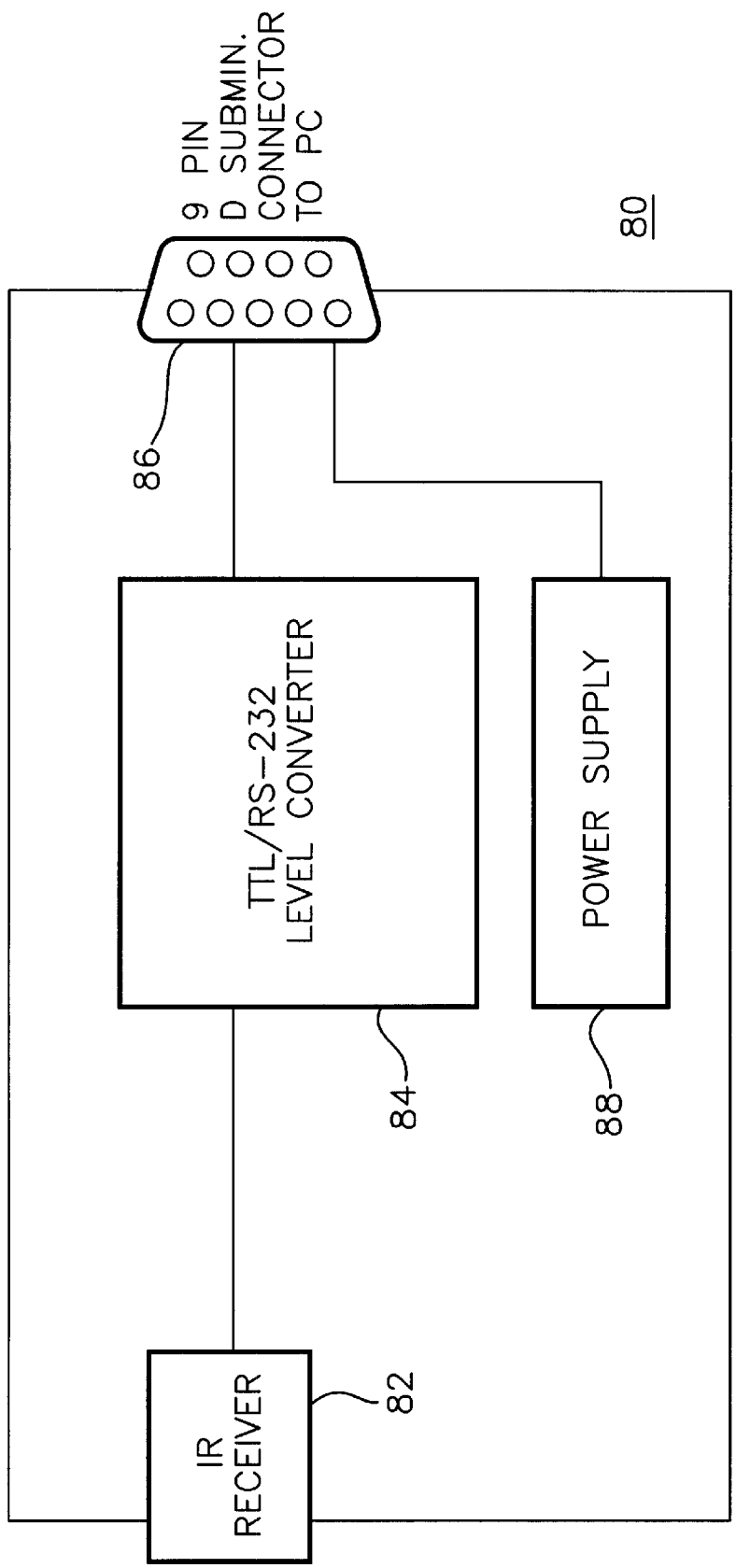
FIG. 8 illustrates an infrared receiving unit according to the present invention.

FIG. 8 schematically illustrates an infrared receiver unit 80 which may be used in conjunction with the above-described infrared transmission unit 50. The infrared receiver module 80. comprises an infrared receiver transducer 82 connected to a TDL/RS232 level converter 84. The converter 84 is connected to a 9-pin D-submin connector 86 which is adapted for connection with a computer means such as a PC or a video game system. It should be understood that a PC 36 may contain a video game. The infrared receiver unit 80 also comprises a power supply 88 which delivers power to the IR receiver 82 through the 9-pin connector 86 and the RS232 converter 84. The IR receiver transducer 82 is capable of handling at least one input signal which corresponds to a respective EEG electrode signal that emanates from the infrared transmission unit 50. Outputs from the IR receiver transducer 80 are directed into the nine-pin connector 86 for further transmission to a PC 36 or video game system. The nine-pin connector 86 provides a standard serial output to the PC 36 or game module. Preferably, the parts count may thus be kept to a minimum.

The microprocessor 62 of the infrared transmission unit 50 is preferably set at a constant data rate transmission, e.g. at 9600 baud. The receiver 80 parses the constant data flow rate for lower FFT sampling frequencies.

Thus, as represented by FIGS. 5, 7 and 8, the present invention is particularly well suited to allow the user to assume any desired posture or position or to engage in any desired movement while engaging in a biofeedback session without being tethered by any connection lines which might hamper the comfort, freedom of movement, relaxation, attentiveness or concentration of the user. For example, the user may recline, stretch, or adjust before, during, or after sessions or phases of sessions of training or playing. Referring again to the illustration of FIG. 6, the present invention may further utilize other modes of input or physical control means 46, such as a computer keyboard or joystick, in conjunction with the transmission of EEG signals by infrared carrier, in providing the user U with feedback.

Figure 9:
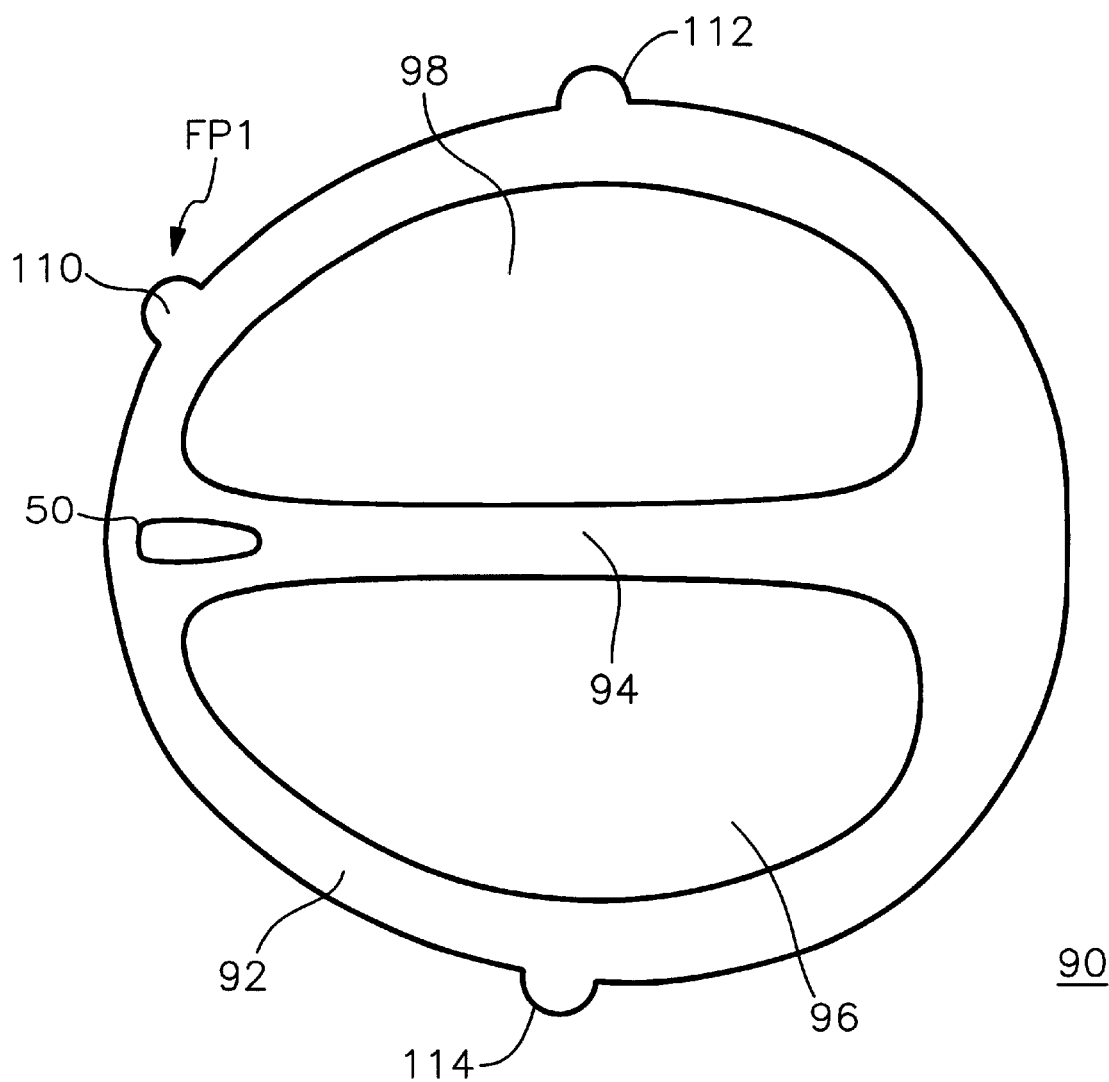
FIG. 9 illustrates a top view of headpiece embodying the invention comprising a particular electrode arrangement.
Figure 10:
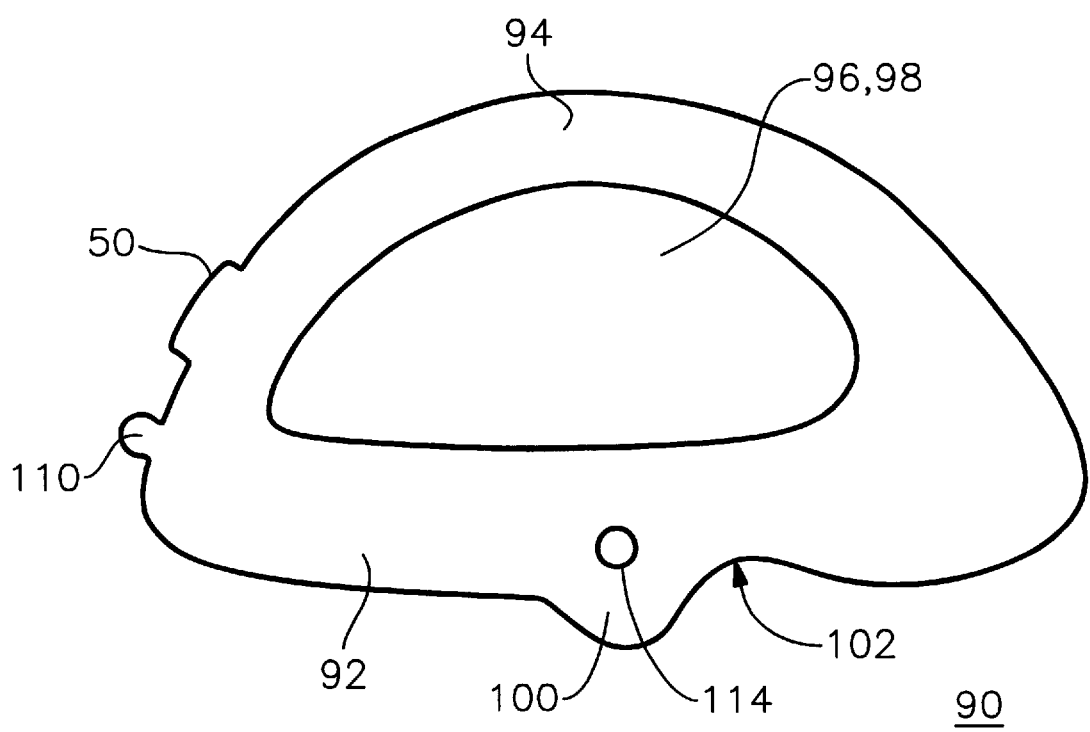
FIG. 10 illustrates a side elevational view of the headpiece of FIG. 9.
Figure 11:
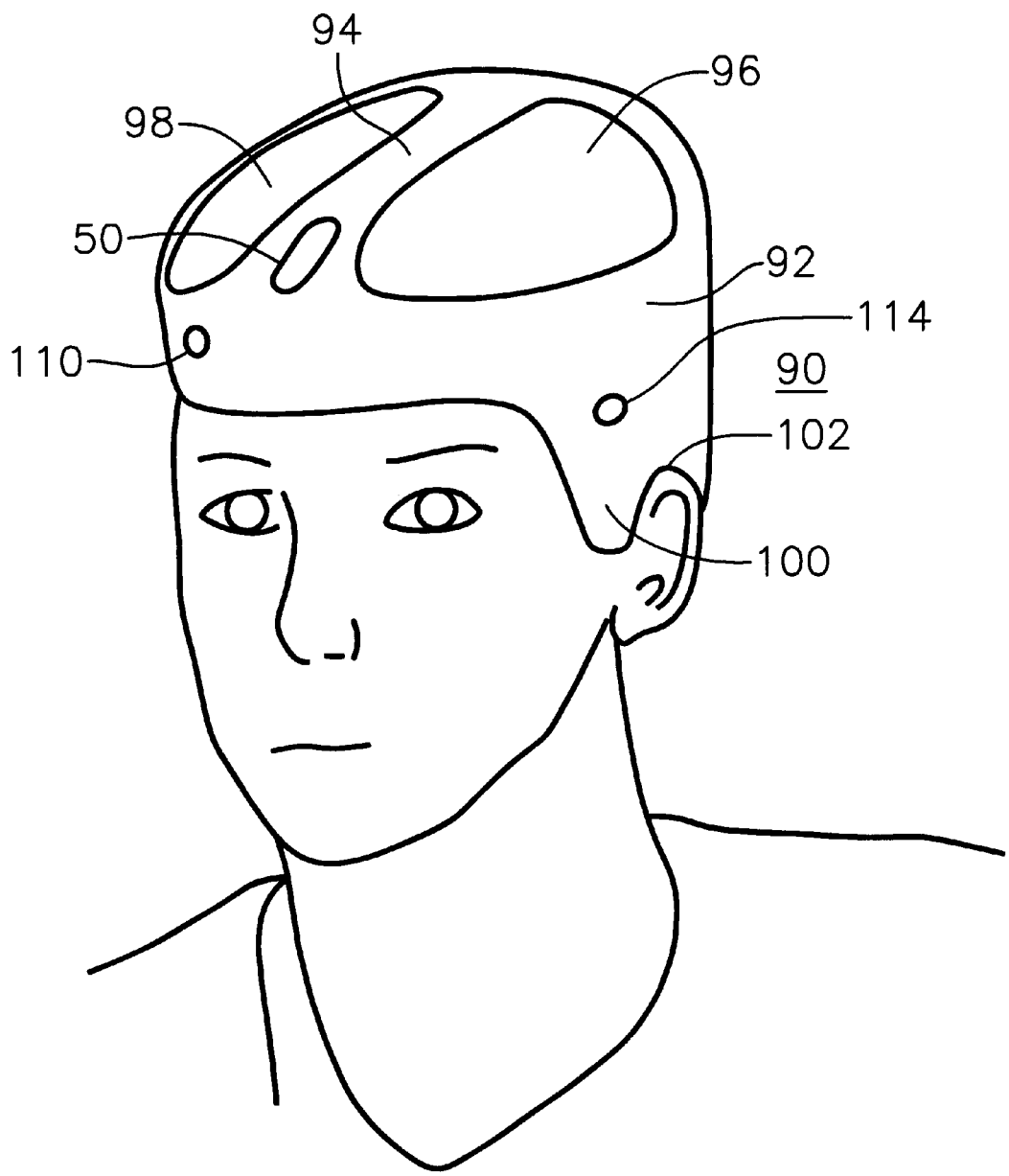
FIG. 11 illustrates a perspective view of the headpiece as worn by a user.

FIGS. 9–11 show an embodiment of a headpiece unit 90.

As best seen in FIG. 9, the headpiece unit 90 comprises a circumferential portion 92 and a medial portion 94. The headpiece 90 is provided with a pair of generally hemispherically-shaped or lobe-shaped openings 96, 98 defined by the circumferential and medial portions 92, 94. As seen in FIGS. 10–11 the circumferential portion 92 further comprises a pair of downwardly extending portions 100 and a pair of opposed upwardly extending indentations 102. The combination of the downwardly extending portion 100 and the upwardly extending indentation 102 are adapted to fit around the ear of a user, thereby at least partially preventing forward or backward movement or rotation with respect to the head of the user. An infrared transmission unit 50 is disposed on the headpiece, preferably on a forward position on the circumferential portion, although the infrared transmission unit may be disposed in another location on the headpiece 90.

In one embodiment, the headpiece unit 90 further comprises three electrodes or sensors for detecting EEG signals from the head of the user. When used in a biofeedback system according to the present invention, at least one electrode a primary electrode 110 is preferably located on the headpiece 90 corresponding at least generally to at least one of the positions on the head of the user which correspond to the FP1 (above the right eye), FP2 (above the left eye), and/or Sensory Motor Rhythm (forward center of head) EEG locations. The headpiece 90 further preferably comprises at least two additional electrodes: a reference electrode 112 and a ground electrode 114, which are disposed in opposite mastoid areas. For example, if FP1 is chosen as a primary electrode 110 site, as shown in FIGS. 9–11 the reference electrode 112 would be disposed at the right mastoid area while the ground electrode 114 is disposed at the left mastoid. Thus, the reference and ground electrodes 112, 114 are positioned on opposite sides of the circumferential portion 92 approximately above the downwardly extending projection. The sensory motor rhythm area is located at the front of the medial portion. If the sensory motor rhythm area is chosen as primary electrode, the reference electrode may be chosen from either mastoid area with the ground electrode disposed opposite the reference.

FIG. 11 illustrates the headpiece unit disposed on the head of a user.

It should be noted that the headpiece 90 may be adapted to receive a plurality of electrodes, even if less than all of the electrodes are electrically connected to the IR transmission unit 50. Thus, the headpiece 90 may be provided with a plurality of holes which accommodate an electrode or electrode tip, and the headpiece 90 may be used even if not all the holes have electrodes disposed therein. It should further be understood that the headpiece 90 further comprises an electrical connection network which is capable of connecting desired electrodes to the IR transmission unit 50. Furthermore, the headpiece may comprise a means for selectively electrically connecting each electrode to the unit 50.

Thus, the headpiece unit or headset unit 90 may be made according to an ergonomic design which is compatible with the head of the user. The headpiece may be made from lightweight material, such as plastic and/or styrofoam. The symmetric openings 96, 98 in the top of the headpiece 90 contribute to a lightweight design, and further provide ventilation and/or heat transfer to the head of the user, thereby providing comfort and promoting relaxation to the user which is especially helpful during attempts to increase concentration or attention. The circumferential and medial portions, including the downwardly extending projections and the upwardly extending indentations in the circumferential portion, provide the user with a snug but comfortable fit which maintains contact between the electrodes and the head of the user without undue weight, pressure, or discomfort to the user.

The electrodes 110, 112, 114 extend inwardly from the inside surface of the headpiece 90. The electrode tips may be fixedly attached thereto. More preferably, the electrodes are releasably attached to the headpiece 90.

Figure 12:
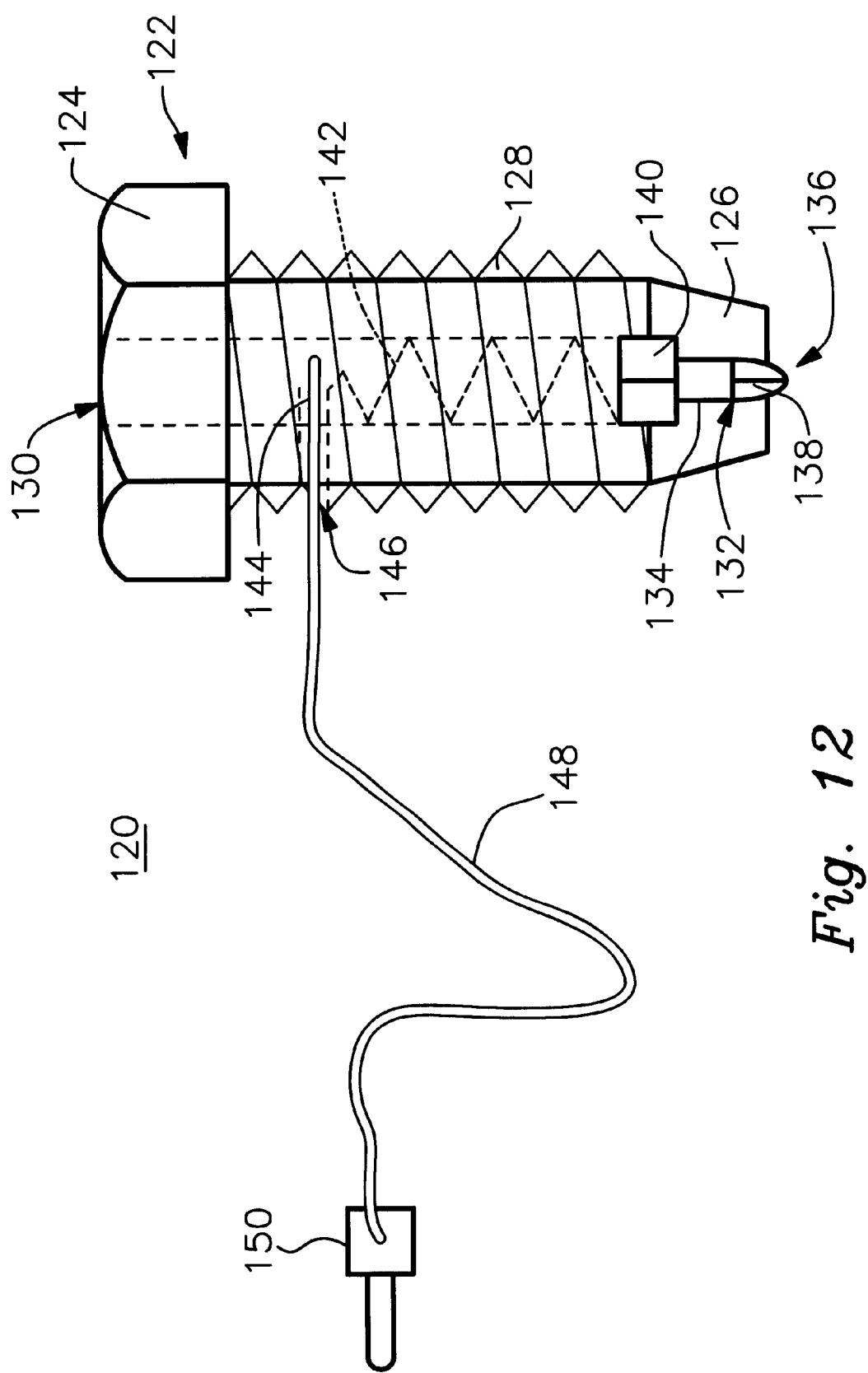
FIG. 12 illustrates a means for releasably mounting an EEG electrode to a headpiece.

FIG. 12 illustrates a preferred embodiment of a means 120 for releasably mounting an EEG electrode on the headpiece 90. A screw 122 having a head 124, a tip 126, and a plurality of threads 128 disposed on the outer surface therebetween, is provided with a bore hole 130 which starts at the top end and extends into the interior of the screw 122 and terminates before reaching the tip 126. A smaller diameter through hole 132, concentric with the bore hole 132, is provided through the tip 126 of the screw 122, wherein an inner shoulder 134 is formed in the interior cavity comprising the bore hole 130 and through hole 132. A probe tip 136 having a narrow diameter portion 138 and a wide diameter portion 140 is inserted into the bore hole 130 at the top of the screw 122, wherein its narrow portion 138 is inserted first. The screw 122 and the probe tip 136 are adapted such that the wide portion 140 of the probe tip 136 rests upon the inner shoulder 134 of the screw 122, and the narrow portion 138 of the probe tip 136 extends through the through hole 132 and projects outwardly from the bottom surface of the screw 122. An electrically conductive, preferably lightweight, compression spring 142 is inserted into the bore hole 130 on top of the probe tip 136, wherein the bottom end of the spring 142 contacts the top of the probe tip 136. An electrically conductive pin 144 is inserted into an opening 146 in the side of the screw 122 for contact with the top end of the conductive spring 142. The pin 144 may extend partially across the bore hole 130 in a cantilever arrangement and have adequate strength to retain the compressive loads imparted by the compression spring 142 and probe tip 136 within the screw 122, e.g. the probe tip 136 may be adapted to withstand cantilever bending moments delivered by the spring 142 and probe tip 136 when the probe tip 136 is pushed back into the screw 122, such as when the bottom of the probe tip 136 is flush with the bottom surface of the screw 122. In another embodiment, the pin 144 may extend fully across the bore hole 130 and be inserted into opposing inner walls of the screw 122. The pin 144 may be substantially round, substantially flat, or some other shape. The pin 144 may be fixedly attached to the screw 122 by adhesive means applied between the pin 144 and the screw 122. The pin 144 may instead be removably attached therefrom, e.g. by providing the pin 144 and screw 122 with mating threads. Alternatively, or in addition, the screw 122 may be provided with a cap which is adapted to fit into the top end of the bore hole 130 and is attached to the remainder of the screw 122 so as to provide a stop means for the compression spring 142 and pin 144. The cap may be fixedly attached to the remainder of the screw 122, for example by an adhesive means applied therebetween, or the cap may be releasably attached to the remainder of the screw 122, for example by providing matching threads on mating surfaces of the cap and the inner wall of the screw 122 which defines the bore hole 130. The pin 144 is then connected to the infrared transmission unit 50, which may be adapted to receive the pin 144 directly, or an additional wire 148, and/or a connecting jack 150 may be provided for connection with the infrared transmission unit 50.

In a particular embodiment, a nylon screw 122 having a coarse thread 128 and a diameter of one half to five eighths inch, is provided with concentric holes 130, 132 drilled out of the center. A stainless steel probe tip 136 with a rounded end is inserted into the cavity. A conductive, lightweight compression spring 142 is inserted behind the probe tip 136.

A conductive pin 144 is inserted into a hole 146 drilled into the side of the screw 122. A probe wire 148 is attached to the conductive pin 146. The entire assembly 120 is mounted into a headpiece 90 or helmet made of suitable material, for example plastic and/or styrofoam, which contains holes drilled therethrough for accepting the assembly 120. Optionally, a nylon nut may hold the screw 122 in place.

Figure 13:
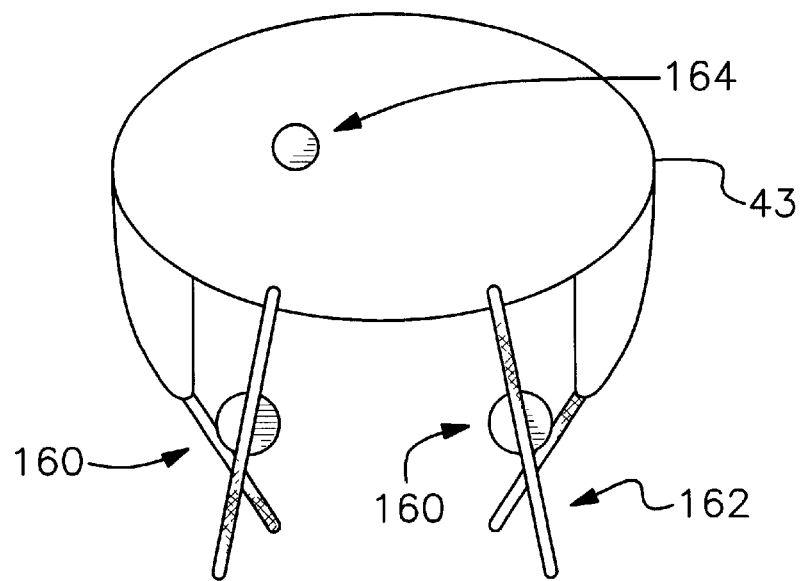
FIG. 13 illustrates an electrode arrangement according to another embodiment of the present invention wherein two electrodes are positioned on the chin straps of a headpiece.

FIG. 13 shows an electrode or sensor arrangement according to another preferred embodiment of the present invention wherein two sensors or electrodes 160 are positioned on the chin straps 162 of a headpiece 43. A top sensor or electrode 164 is preferably internally mounted on the headpiece 43. The headpiece 43 may be, for example, the helmet or headpiece as depicted in FIGS. 7, 9, 10, or 11, as well as other headpieces or the like known to those skilled in the art. Thus, the top electrode or sensor 164 may be held in a desired position in relation to the head of a user by an appropriate headpiece. In this embodiment, two other electrodes or sensors 160 are provided on the respective chin straps 162 of the headpiece 43. In another particular embodiment, the headpiece 43 may have a single chin strap which spans the lower portion of the head of the user, e.g. around or under the chin, so that the two other electrodes 160 may be disposed on the single chin strap at different locations. The chin strap thus preferably promotes contact between the head of the user and the two other electrodes 160, as well as with the top electrode 164 by virtue of the securement of the headpiece to the user by means of the chin strap or straps.

Figure 14:
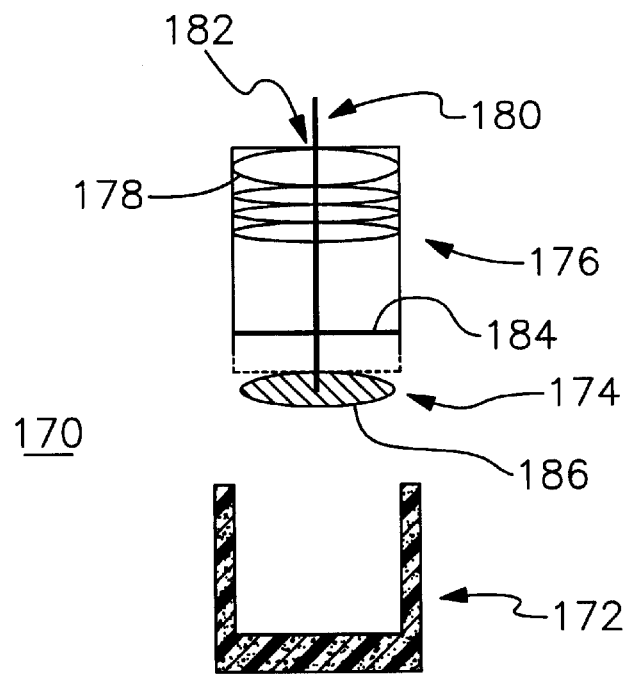
FIG. 14 illustrates an elevational cutaway view of another embodiment of an electrode sensor of the present invention, wherein the sponge cover is shown exploded from the remainder of the electrode.

FIG. 14 illustrates an elevational cutaway view of another preferred embodiment of an electrode sensor 170 according to the present invention. A sponge cover 172 is shown exploded from the remainder of the sensor 170. An electrode 174 is movably disposed within a housing, shown as a cylindrical housing 176. The cylinder 176 may advantageously be made of plastic, for example, for light weight and resistance to moisture. The housing 176 contains a spring 178 for biasing the electrode 174 out of the housing 176. The spring 178 is attached to the stem 180 of the electrode 174. The distal end of the stem 180 of the electrode 174 extends out of an opening 182 provided in the housing 176. An insert 184 attached to the stem 180 contacts part of the housing, or part of the housing 176 contacts the spring 178 and/or the electrode 174, for engagement therewith to contain the spring within the cavity formed in the housing 176 and to limit the travel of the electrode 174. The proximal end of the electrode 174 contacts the user. The proximal end is shown with a contact plate 186 for sensing electrical activity from the user. The contact plate 186 is preferably made from silver/silver chloride or tin, or another suitable conductive material. A sponge cover 172 is provided which fits over the contact plate 186. Gel or a saline solution is preferably contained on or within the sponge cover 172, thereby providing a means for enhancing contact with the user and conducting of electrical activity therethrough, thereby defining an electropatch means. Thus, when the sensor is positioned in proximity to the user, the spring loaded electrode 174 helps to maintain contact with the user even in the event of relative movement between the sensor and the user. Furthermore, the sponge cover 172 impregnated or covered with gel or saline solution provides an electropatch or a resilient contact mount between the user and the sensor 170, so that increased contact and conductivity can be achieved by compression of the sponge cover 172 against a part of the user. It should be understood that the sensor 172 of FIG. 14 may be held in place against the body or head of the user by a headpiece, helmet, or other variety of apparatus, clothing, or other means.

Training Paradigm

The apparatus described hereinabove, with appropriate programming, can be employed to implement educational protocols as described hereinbelow for attention training. The implementations have a resemblance to computer games, but actually are educational exercises. More particularly, various ones of the educational protocols can be employed to teach and improve various educational skills.

During operation, averages of theta and beta activity are obtained during a forty-five second period to establish a baseline. The user's theta thresholds are then set at 1 to 2 millivolts below their average millivolt theta activity, and beta thresholds are set at the average millivolt beta activity levels. (These millivolt levels refer to signal levels after application.) This allows the user to immediately perceive his level of attention during a session. The beginning and ending thresholds are stored along with scoring data from each educational exercise, and can be later retrieved for progress analysis.

The paradigm encourages the decrease of theta wave activity and increase of beta wave activity by providing rewards after the user achieves 1 to 2 millivolts decrease in theta and 1 to 2 millivolts increase in beta activity.

The feedback is auditory tones and visual graphics in the form educationally based exercises. Further token reinforcement is supplied by on screen scoring. For example, in the Diver game described hereinbelow with reference to FIG. 17, the user can make a fish dive to the bottom of a video ocean as theta thresholds are decreased and beta increased thus scoring higher points on screen. Any increase in theta activity causes the fish to go the opposite direction necessary to score points. When the user achieves over 25 rewards per minute consistently, his threshold (either theta or beta) is made more difficult.

Apparatus responses to theta and beta wave activity as well as the reward system are incorporated for the purpose of educating the user about the attentive state. Thus the primary goal is not to change the EEG (the clinical application), but to provide the basis of educational processes necessary to become successful in the learning environment. Therefore, the educational protocols focus on the following educational components/skills:

(1) attention;
(2) visual tracking;
(3) time on-task;
(4) short-term memory data sequencing;
(5) visual discriminatory processing; and
(6) auditory discriminatory processing.

The successes immediately obtainable in the training paradigm provide motivation for behavioral changes to be instituted by a teacher/trainer/coach. Specifically, these changes refer to reducing or extinguishing behavior not conducive to learning. This is accomplished through reward and success, not punishment. The user maintains a vested interest in outcomes by charting all progress.

Figure 15:
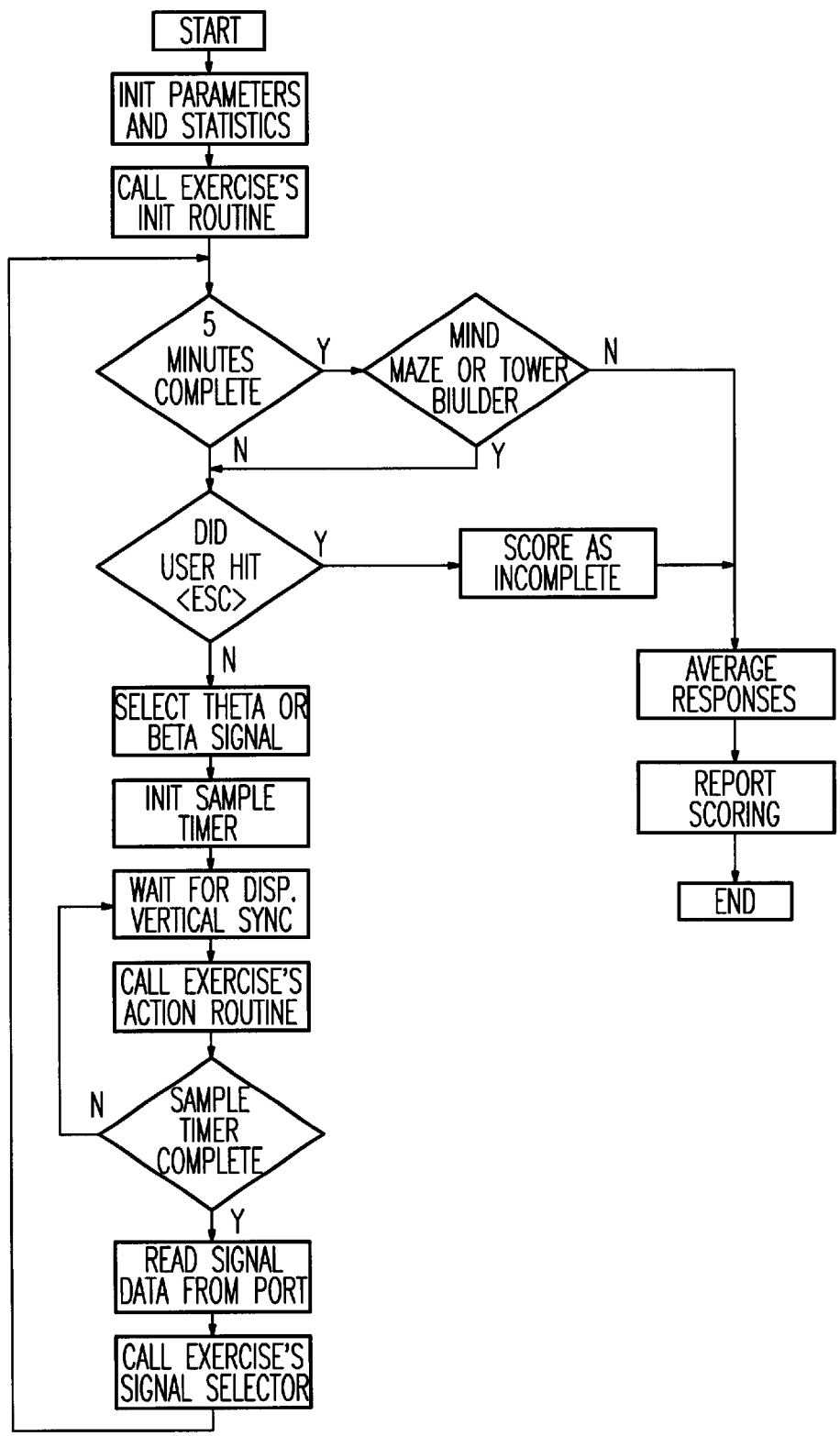
FIG. 15 is a generalized program flowchart.

FIG. 15 is a generalized program flowchart of implementations of various educational exercises described hereinbelow with reference to their own more particular flowcharts.

Educational Protocols

The educational protocols are organized into six levels corresponding to the six educational components or skills listed above. For each level there is at least one educational exercise.

The apparatus includes a recording device in the form of computer memory and storage devices. For each of the exercises the computer measures and saves to the recording device the performance data of individual users including score, duration of play, and average focus and cognitive processing levels; and the computer accumulates and saves to the recording device the cumulative time on-task of individual users.

In many exercises, to further challenge the ability of the user to maintain a focused state, visual distractions on the display, or audible distractions, or a combination of both are employed.

In all implementations, electrical activity of the brain of the user. is monitored to obtain at least one signal (which may exist in software) having a value indicative of a level of focus, which is compared to a reference threshold value (which likewise may exist in software) to generate an on-task signal (which also may exist in software) when at least a threshold level of focus is indicated. Likewise a cognitive processing signal may be obtained and processed.

Level I

Figure 16:
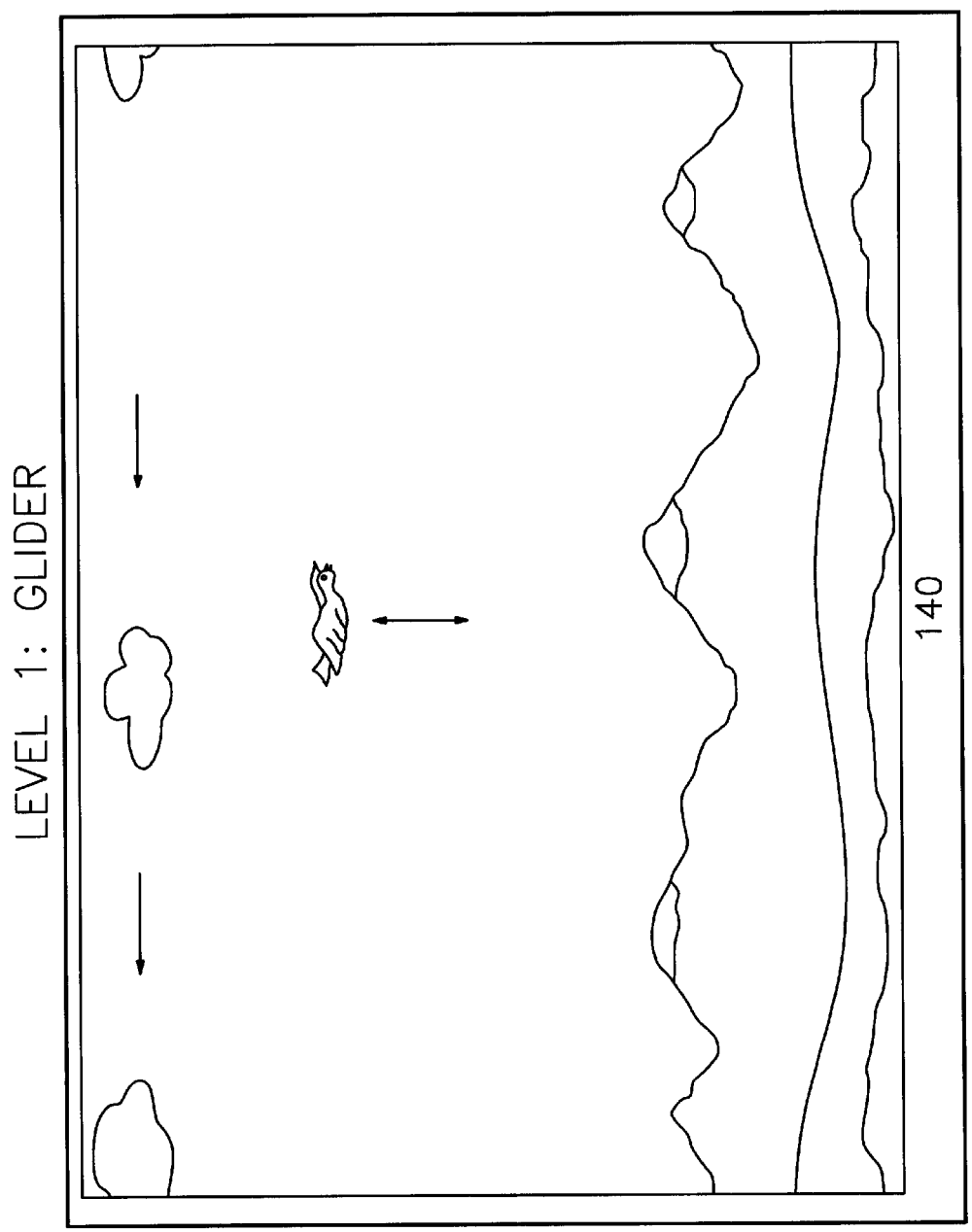
FIG. 16 is a representative screen display of an educational exercise named "Gilder;"
Figure 17:
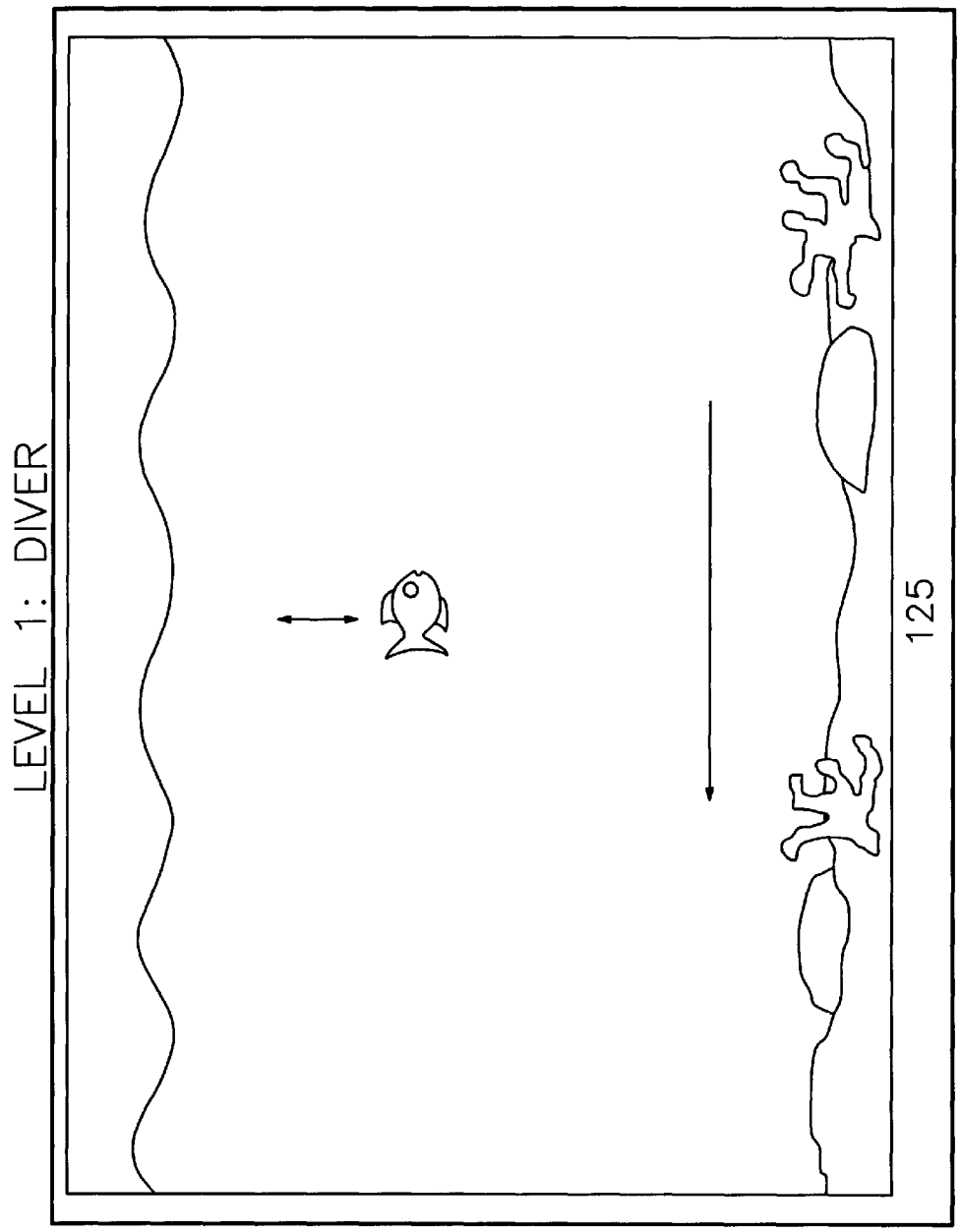
FIG. 17 is a representative screen display of an educational exercise named "Diver;"
Figure 18:
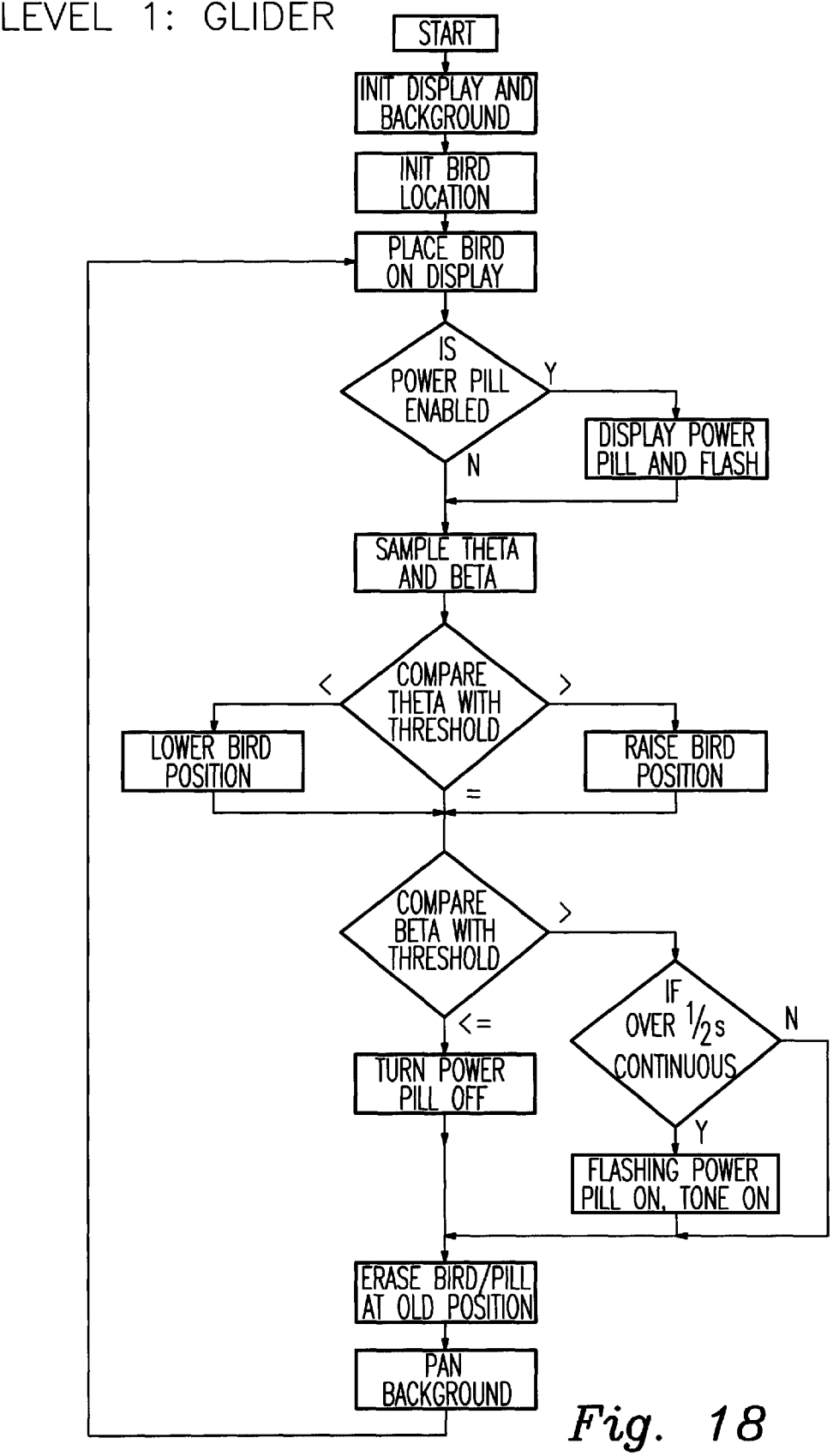
FIG. 18 is an exemplary program flowchart for implementing the "Glider" educational exercise.

FIGS. 16 and 17 represent screen displays of two educational exercises embodiments named "Glider" and "Diver," respectively. Although they are educational exercises, "Glider" and "Diver," as well as the other exercises described hereinbelow, are presented to the user in the guise of games. FIG. 18 is an exemplary program flowchart for implementing the FIG. 16 "Glider" exercise.

Educational Objective: Basic learning of techniques for using the apparatus.

Goal: To gain mastery of the basic attention processes necessary to successfully use the apparatus in other education applications.

Procedure: The user is coached while using the apparatus. The games Glider and Diver are played for five minutes each. These simple games allow the user to control the directions of screen objects or character (a bird, fish, etc.) by attention alone. If focus is not maintained, the screen character moves in the opposite direction necessary to achieve success. The user experiences the attentive state in real time. The process teaches the user to gain control of the software and therefore the attentive state. Relaxation and awareness are stressed.

The FIG. 16 Glider is a bird that moves up and down on the display screen against a horizontally moving background that produces the appearance of motion. The bird object sails to the top of the screen just below the clouds if attention is maintained to a high degree. If a proper baseline was obtained, the bird begins just above the mountains. The greater the attention of the user, the higher the bird soars. The bird flashes and receives power pills as reward for greater attention levels and for higher levels of cognitive processing. A counter keeps-score at the bottom of the screen.

The FIG. 17 Diver is a fish that swims to just above the ocean floor if attention is maintained to a high degree. If a proper baseline was obtained, the fish begins at the very top of the screen. The greater the attention of the user, the lower the fish swims. This gives the user feedback related to the degree of attention paid. It is not important that the user mentally push the fish to the bottom of the screen. It is important to push the fish as low as the user can comfortably accomplish that particular session. It is equally important to encourage the user to maintain the higher level of attention as long as possible. This may be a matter of seconds or perhaps longer intervals. The fish flashes and receives power pills as reward for greater attention levels and for higher levels of cognitive processing. A counter keeps score at the bottom of the screen.

Level-II

Figure 19:
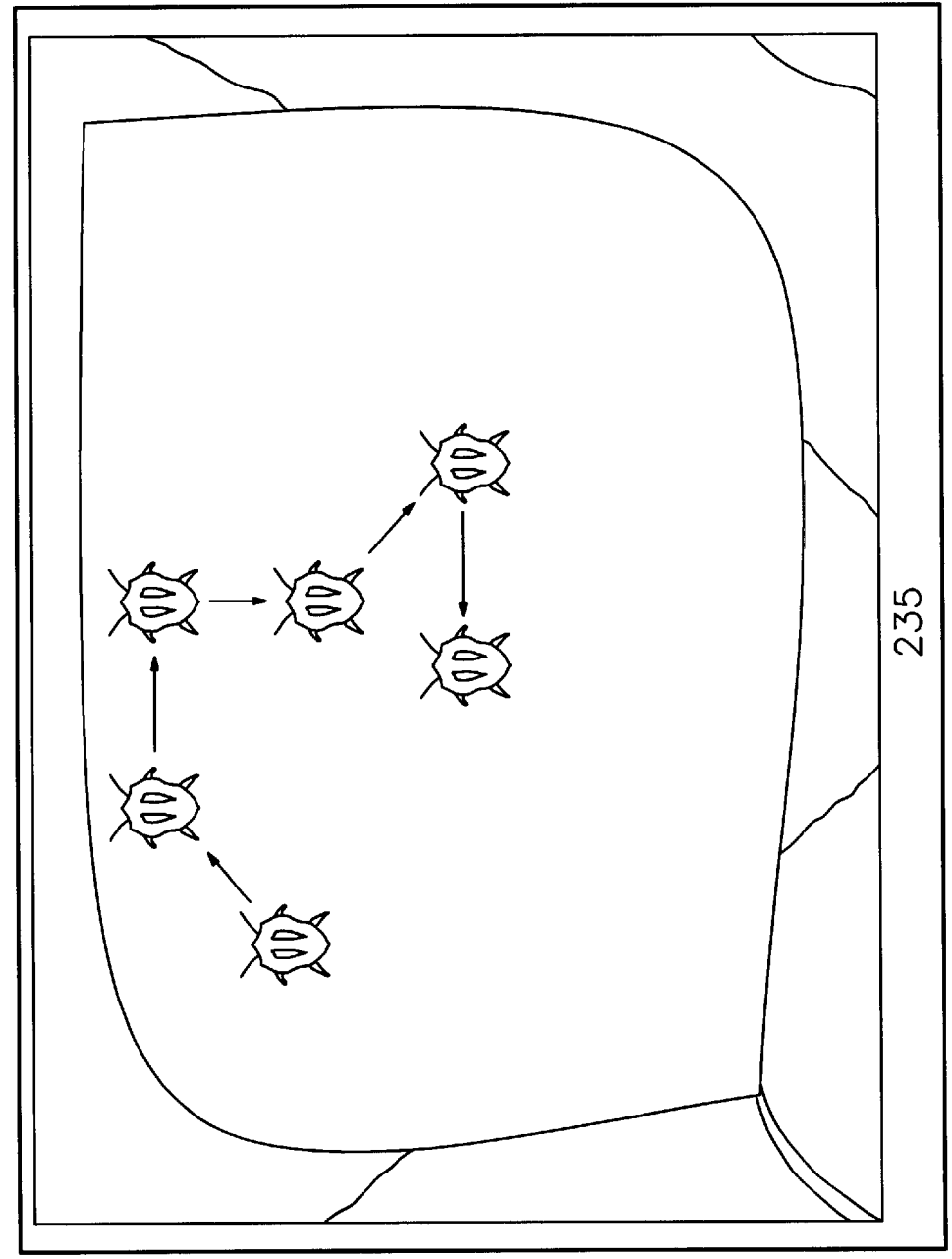
FIG. 19 is a representative screen display of an educational exercise named "Skitter;"
Figure 20:
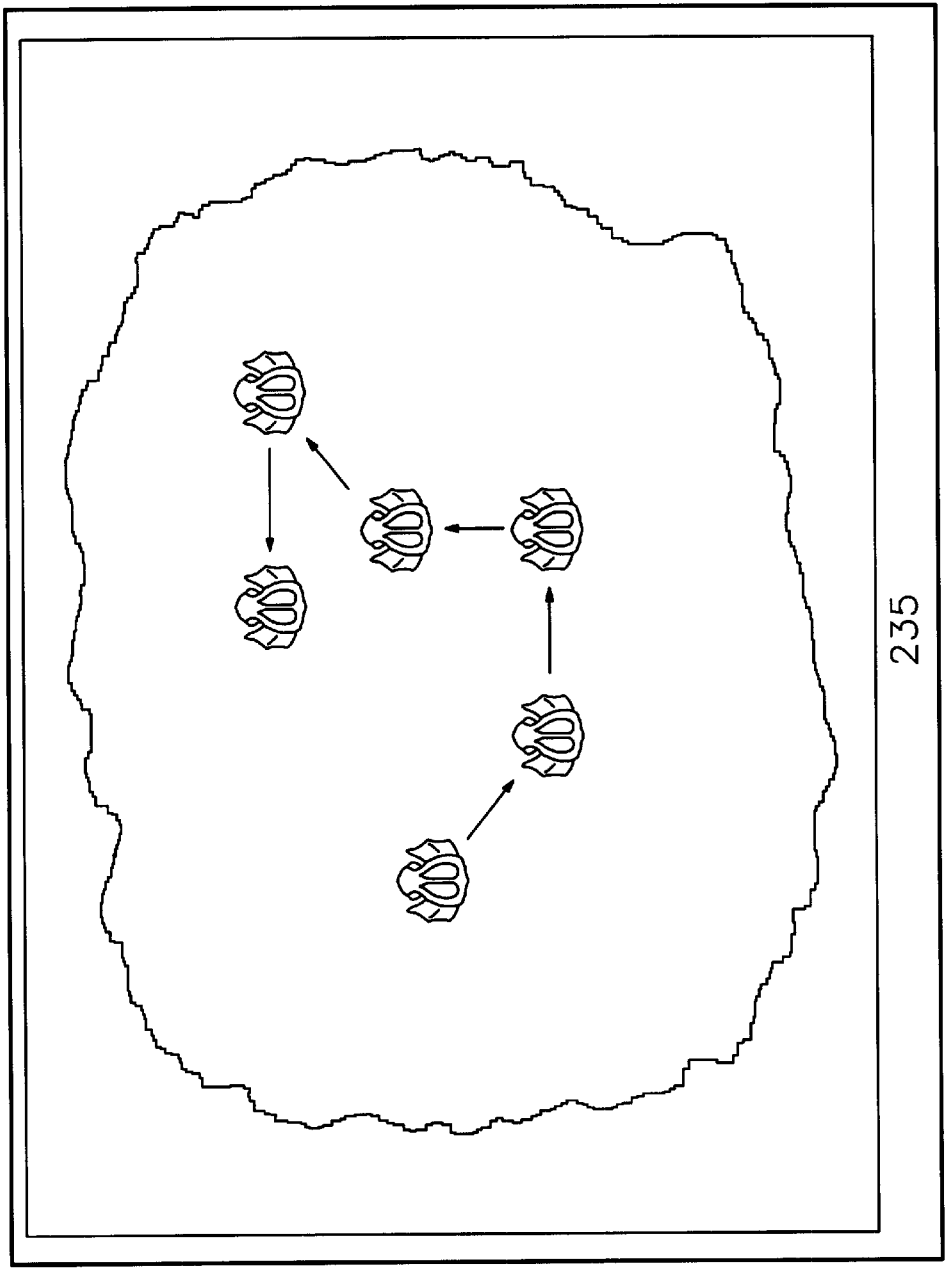
FIG. 20 is a representative screen display of an educational exercise named "Hopper;"
Figure 21:
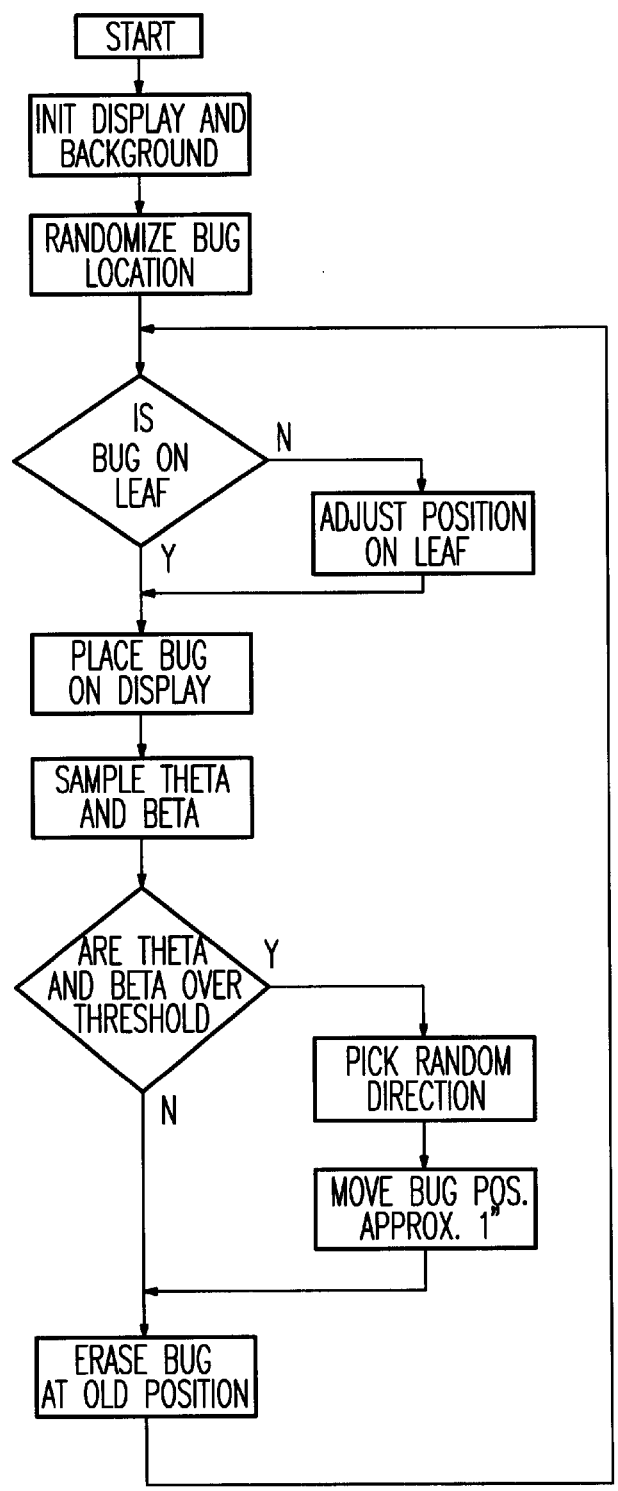
FIG. 21 is an exemplary program flowchart for implementing the "Skitter" educational exercise.

FIGS. 19 and 20 represent screen displays of two educational exercise embodiments named "Skitter" and "Hopper." FIG. 21 is an exemplary program flowchart for implementing the FIG. 19 "Skitter" educational exercise.

Educational Objective: Visual Tracking through Heightened Attention.

Goal: To teach the user to maintain maximum attention while visually tracking a moving object.

Procedure: The user views either a bug on a leaf or a frog on a lily pad. When maximum attention is attained, the screen object or character randomly moves to a new position on the screen. The user is given 5 points and auditory feedback for each new move, thus providing rewards for the ability to track a moving target and maintain focus. The number of moves the user can produce as well as user's score are calculated and stored by the computer. This procedure teaches focus on a moving object to supplement teacher proximity control of attention in a teaching/learning situation.

The FIG. 19 Skitter is a bug that is mentally pushed around the screen by the use of higher attention levels and higher levels of cognitive processing. The bug moves over a pad in random motion. If a proper baseline was obtained, the bug begins in a stationary position. The greater the attention of the user, the more quickly the bug moves. This gives the user feedback relating to the degree of attention paid. It is not important that the user mentally push the bug very fast around the screen. It is important to prompt the user to mentally push the bug as quickly and as much as the user can comfortably accomplish that particular session. It is equally important to encourage the user to maintain the higher level of attention for as long as possible. This may be a matter of seconds or perhaps longer intervals. The bug beeps as reward for greater attention and cognitive processing. A counter keeps score for the user.

The FIG. 20 Hopper is a frog that is mentally pushed around the screen by the use of higher attention levels and higher levels of cognitive processing. The frog moves over a pad in random motion. If a proper baseline was obtained, the frog begins in a stationary position. The greater the attention of the user, the more quickly the frog moves. This gives the user feedback relating to the degree of attention paid. It is not important that the user mentally push the frog very fast around the screen. It is important to prompt the user to mentally push the frog as quickly and as much as the user can comfortably accomplish that particular session. It is equally important to encourage the user to maintain the higher level of attention for as long as possible. This may be a matter of seconds or perhaps longer intervals. The frog beeps as reward for greater attention and cognitive processing. A counter keeps score for the user.

Level III

Figure 22:
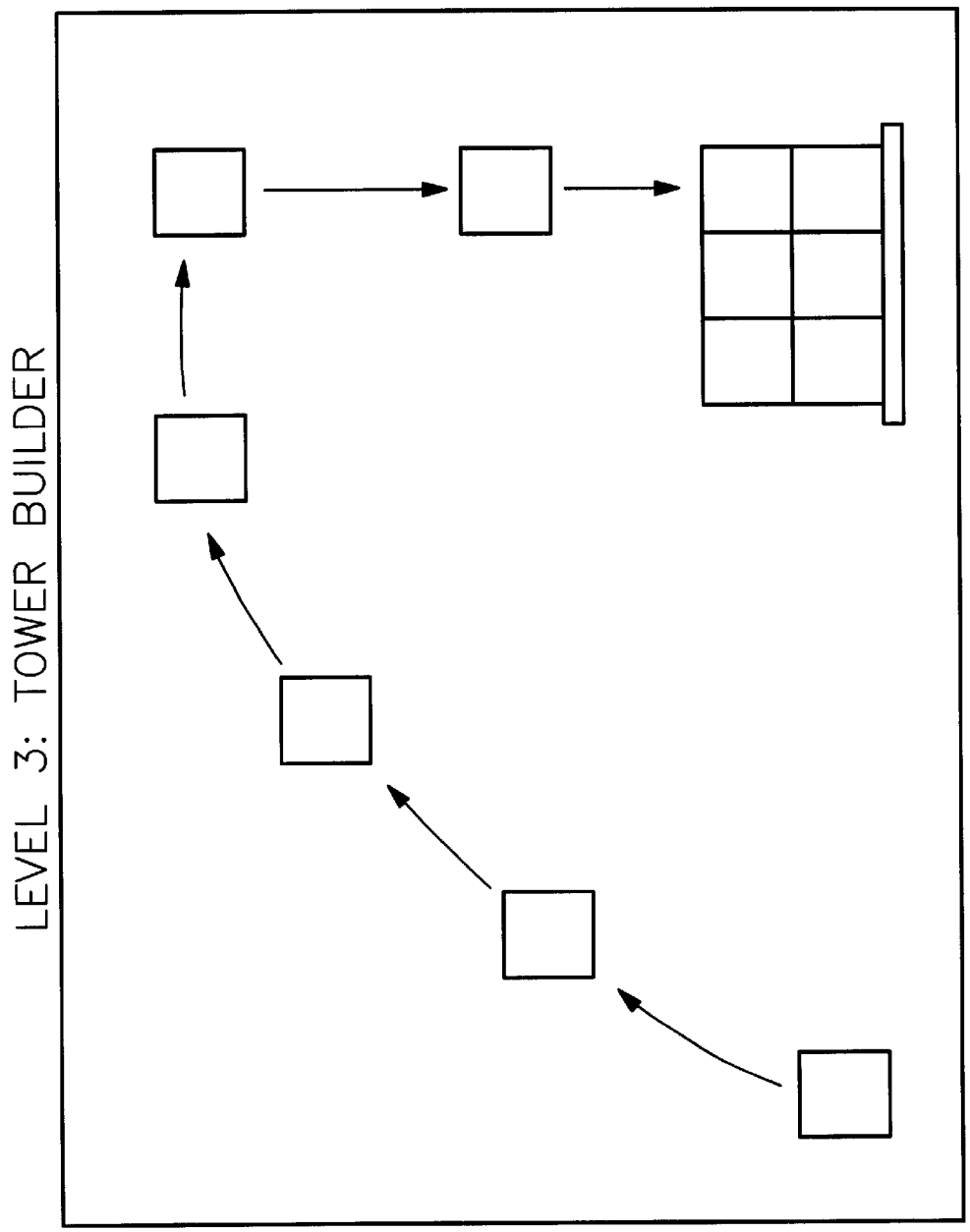
FIG. 22 depicts an educational exercise named "Tower Builder;"
Figure 23:
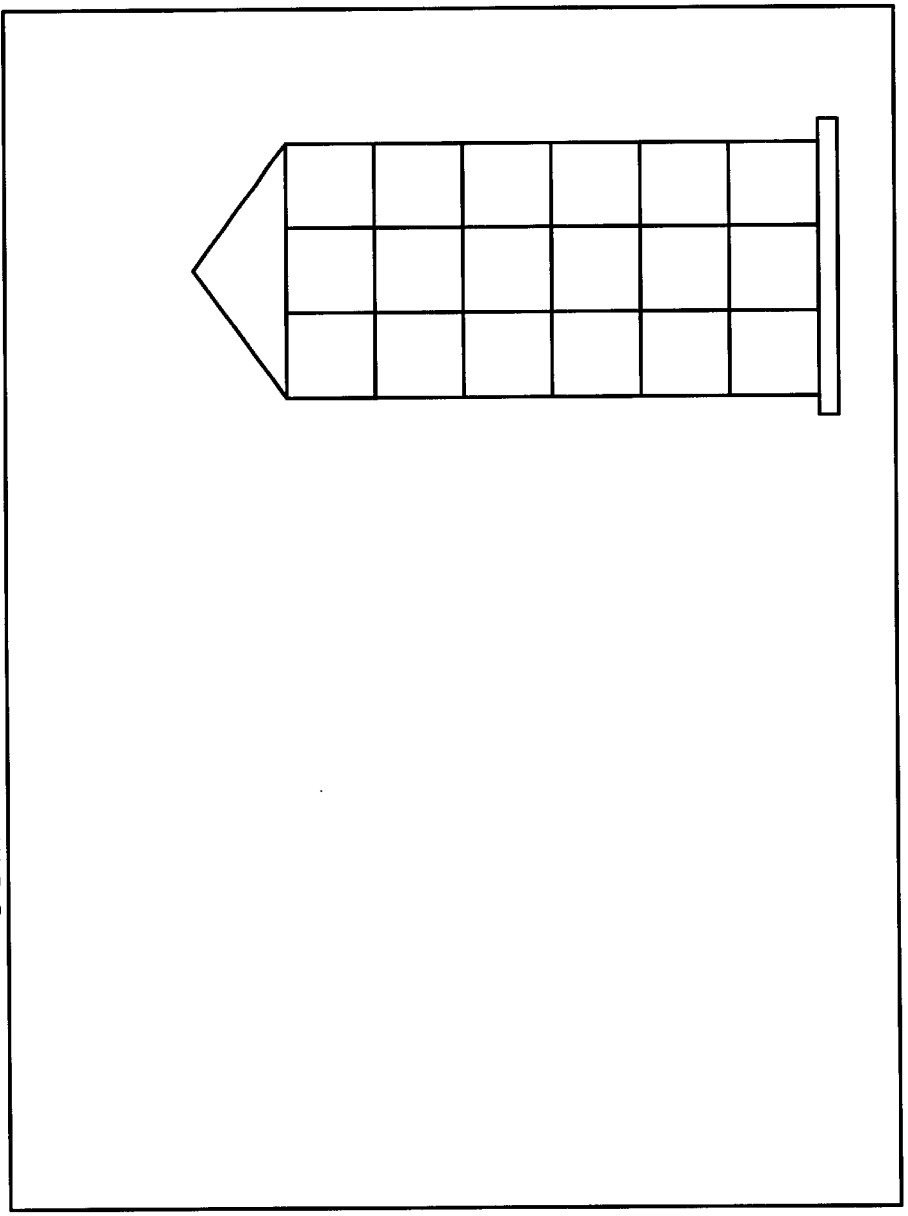
FIG. 23 is a representative screen display of the "Tower Builder" educational exercise at the point of task completion.
Figure 24:
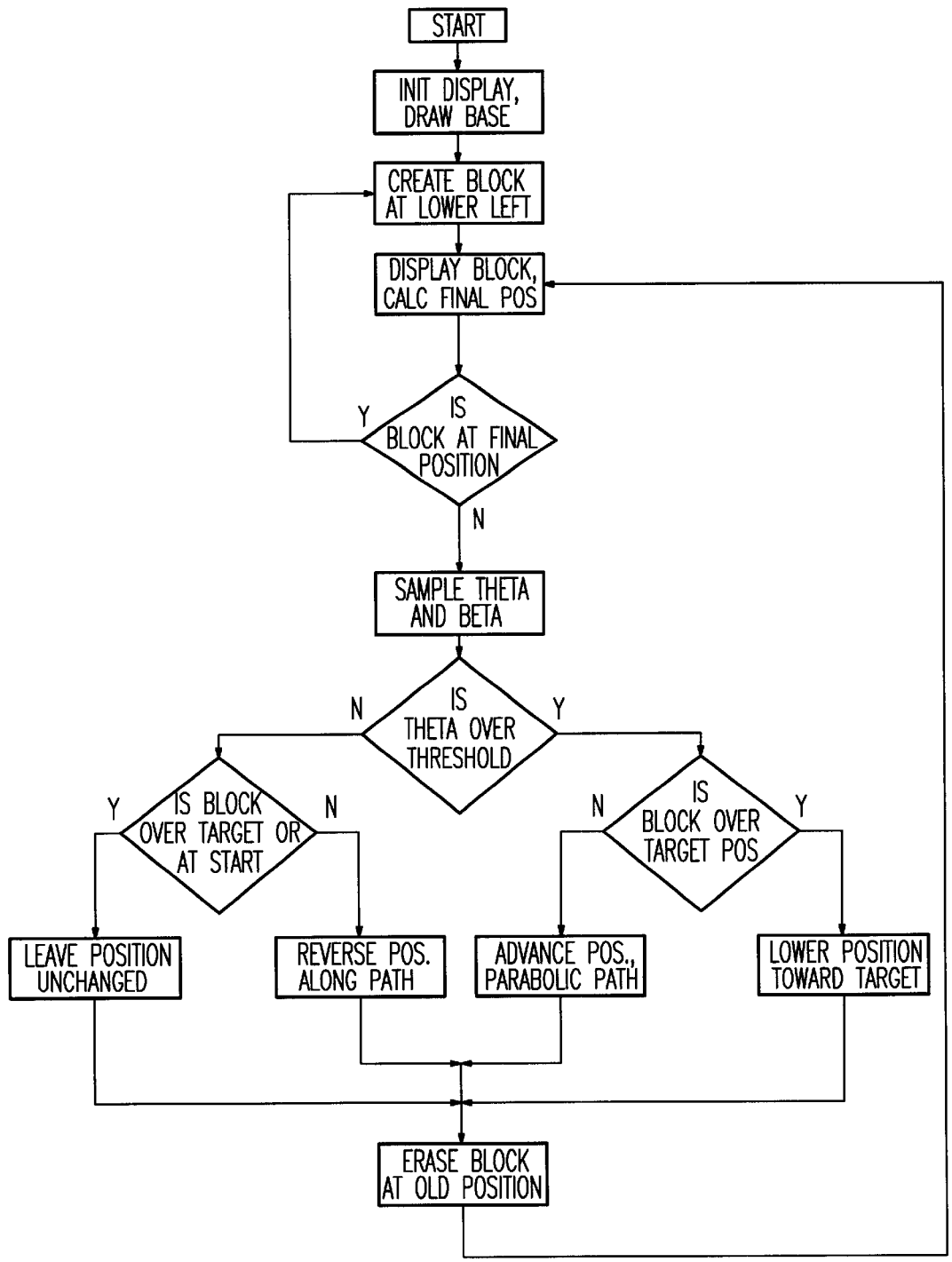
FIG. 24 is an exemplary program flowchart for implementing the "Tower Builder" educational exercise.

FIGS. 22 and 23 depict an educational exercise named "Tower Builder." More particularly, FIG. 22 depicts successive positions along a path of a discrete element in the from of a block object being used to build a structure which happens to be a tower. Although FIG. 22 shows multiple blocks along the path beginning at the lower left corner, these are successive positions of a single block along the path. FIG. 23 represents a screen display of a completed tower. FIG. 24 is an exemplary program flowchart for implementing the Tower Builder exercise.

Educational Objective: Increasing time on task and attention through closed-end tasking.

Goal: For the user to complete a task within a set amount of time by maintaining maximum attention to the screen game.

Procedure: The user is motivated to pay attention for longer time periods by actively paying attention to the games in Level III because the games require task completion. Success is achieved by mentally moving blocks on the left side of the screen to the right side of the screen to build a tower. This can be accomplished only if attention is maintained until completion of construction at which time the user is allowed to proceed to the next level. If the student falls off-task, the blocks either stop moving or move in the opposite direction necessary to complete the task. Three different levels, each respectively increasing in level of sophistication, allow higher scores to be attained with appropriate attention levels. If the user is unsuccessful, the software reduces the level of attention necessary for success. Thus, the next attempt is slightly easier and produces a successful training round. Five minutes play time with success allows user to proceed to next Phase. An analysis of game data compared to time on task is stored for charting user progress.

Level IV

Figure 25:
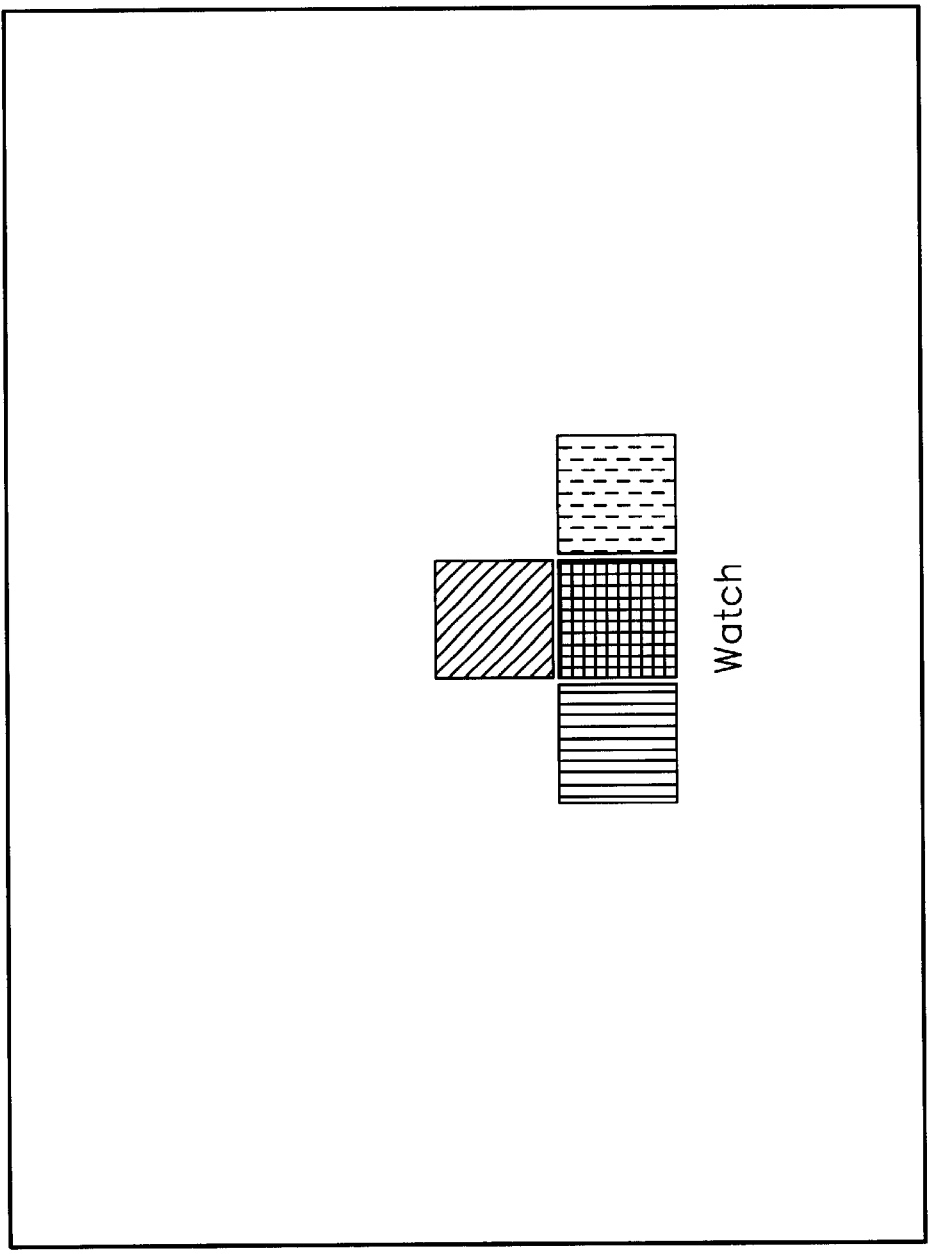
FIG. 25 represents a screen display of an educational exercise named "Mind Maze;"
Figure 26A:
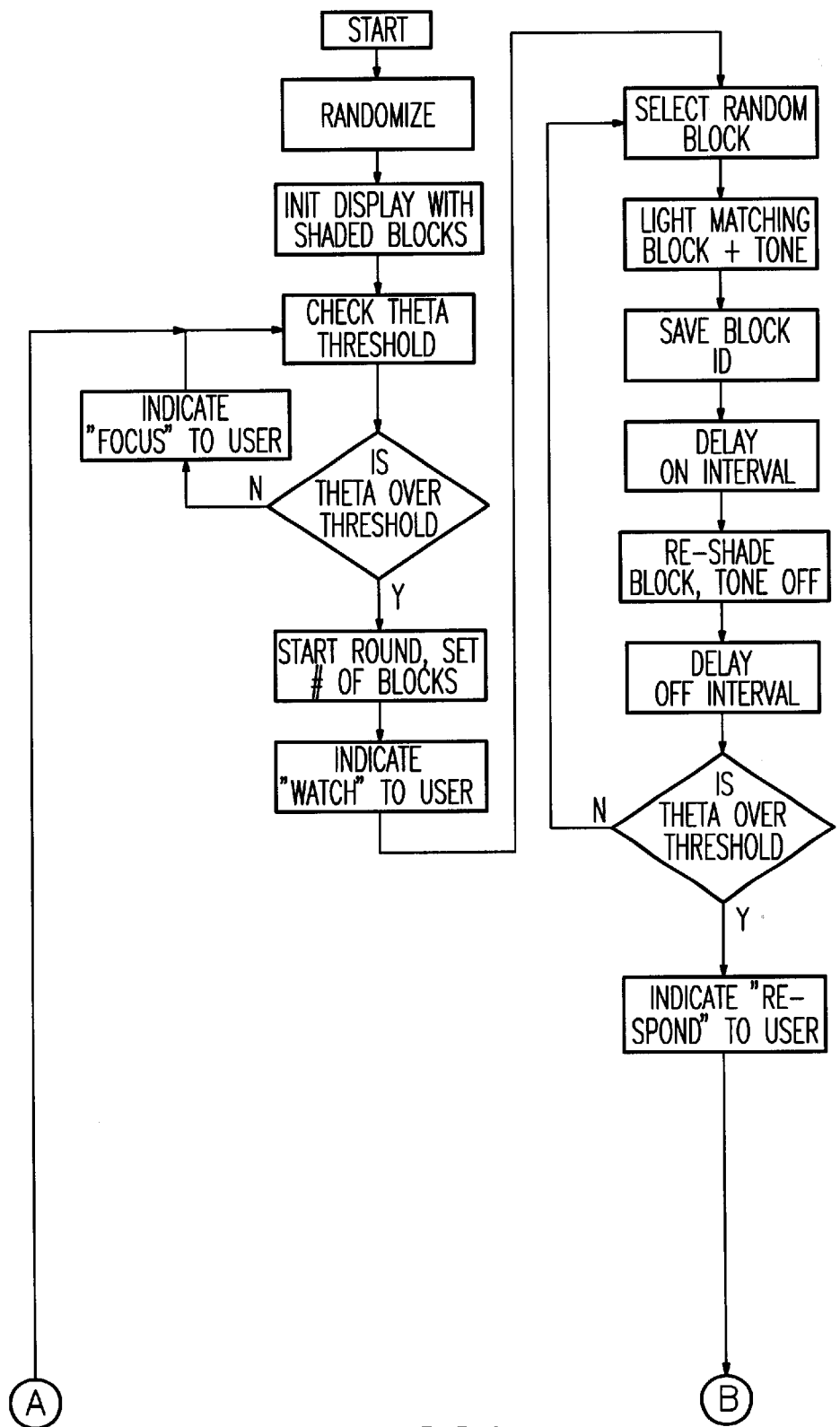
FIGS. 26A and 26B together are an exemplary program flowchart for "Mind Maze;"
Figure 26B:
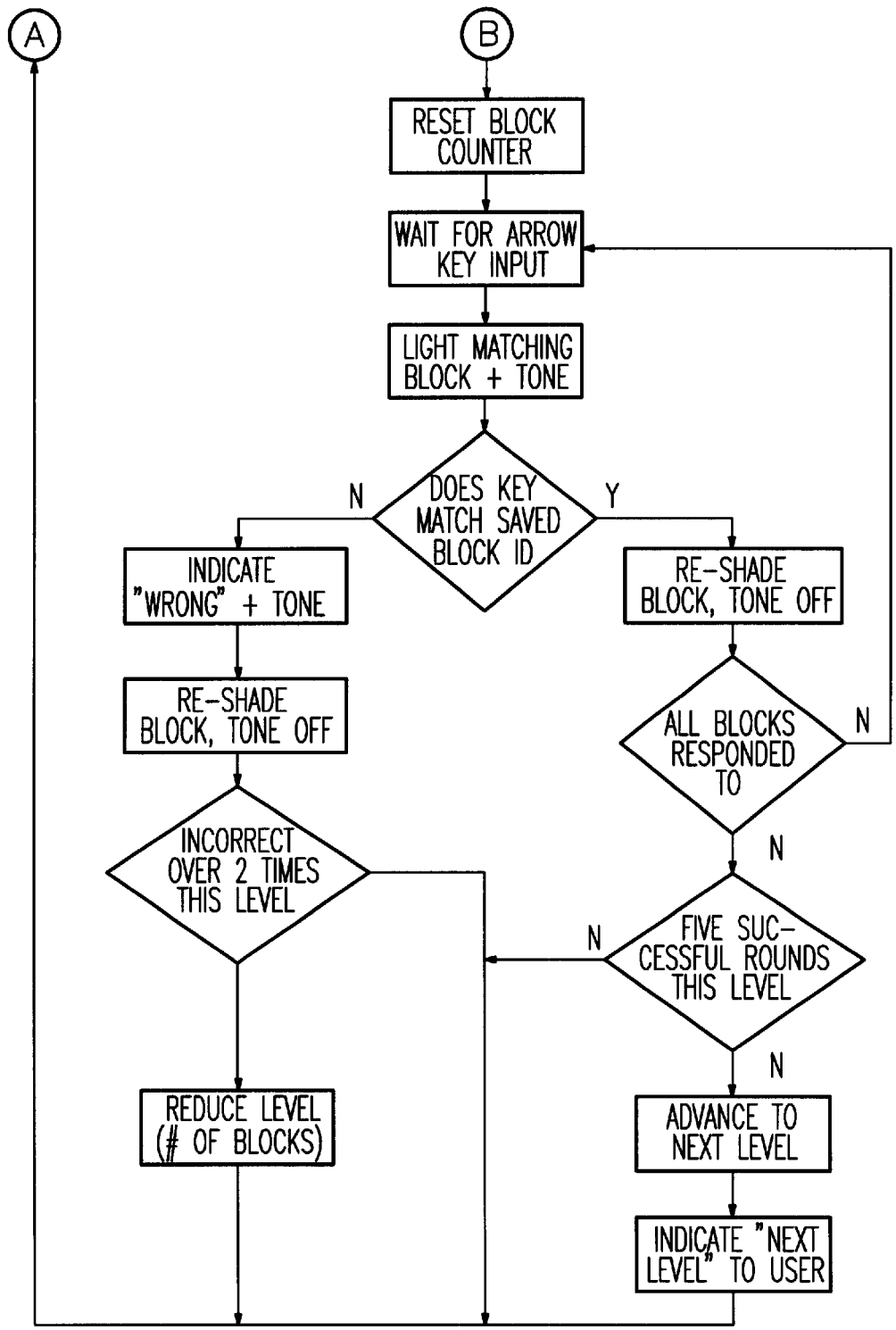

FIG. 25 represents a screen display of an exercise named "Mind Maze," and FIGS. 26A and 26B together are a corresponding exemplary program flowchart.

Educational Objective: Visual and auditory sequencing of data through maintained heightened attention (short-term memory data sequencing).

Goal: User increases attention while selectively attending to appropriate visual and auditory stimuli through pattern matching of visual and auditory patterns.

Procedure: Using the game Mind Maze, the user views a screen with four-color prompts each corresponding with an audible tone. The color prompts visually correspond to the arrow keys-on a standard keyboard. When the appropriate attention level is maintained, the software activates a color and sound pattern. While maintaining an optimum attentive state, the user is prompted by the software to reproduce the auditory tones and color pattern on the computer keyboard arrow keys in sequences of 2 to 15 tones and colors. The greatest sequence data and incorrect attempt data are stored for analysis of user progress in upcoming sessions. This phase teaches the user to pay increased levels of attention while incorporating short-term memory sequencing. This task is very similar to taking notes while listening to a lecture or performing multiple instructions in sequence.

In a variation, characters are displayed on the display screen in random sequences, and the user is promoted to repeat each sequence from memory. To add further difficulty to the exercise, and have added distraction for the user, the characters may be presented at random locations on the display screen. Any available keyboard characters can be displayed in this variation. Again, an appropriate attention level must be maintained.

Level V

Figure 27:
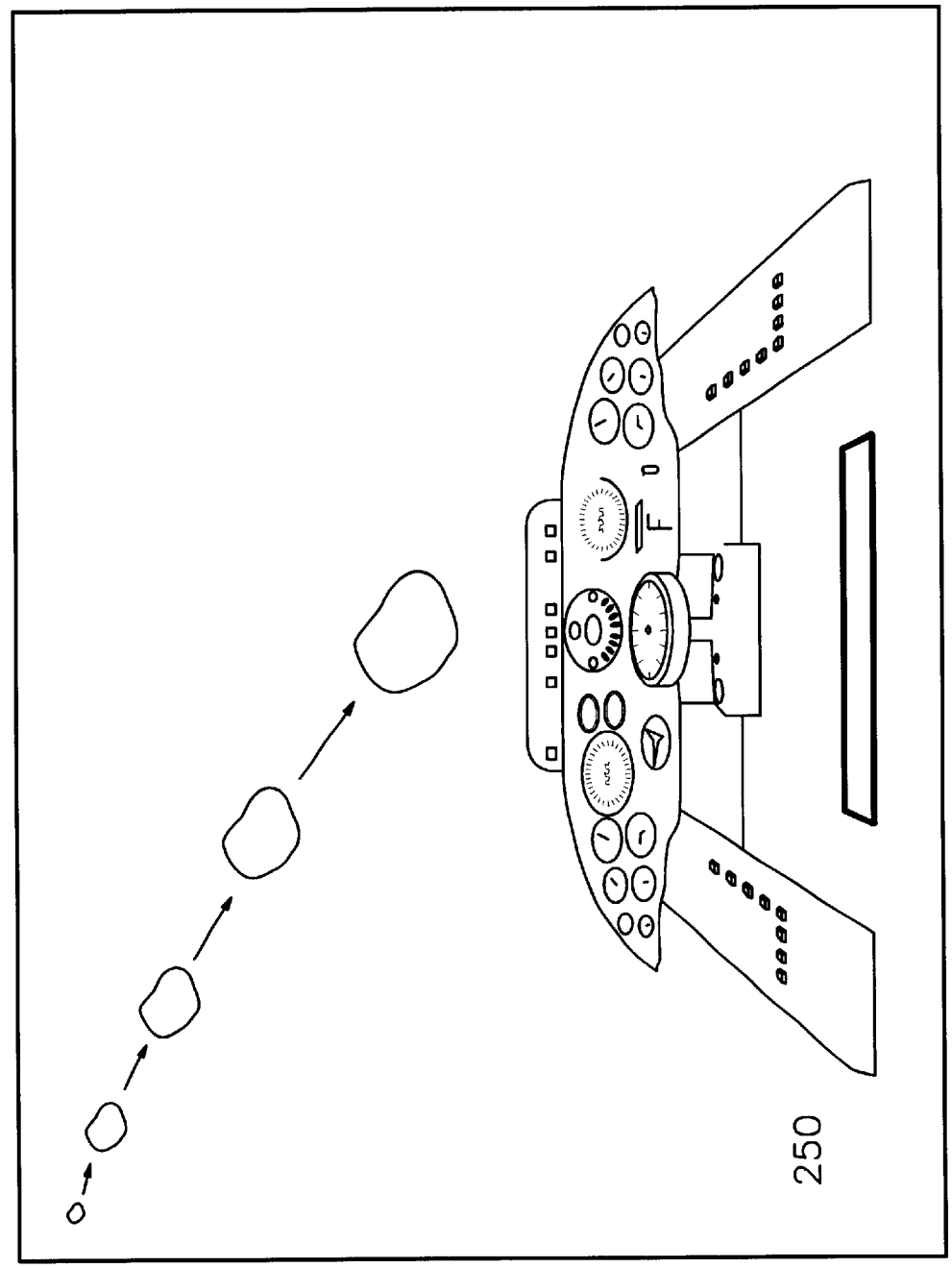
FIG. 27 represents a screen display of an educational exercise named "Starflyer;"
Figure 28A:
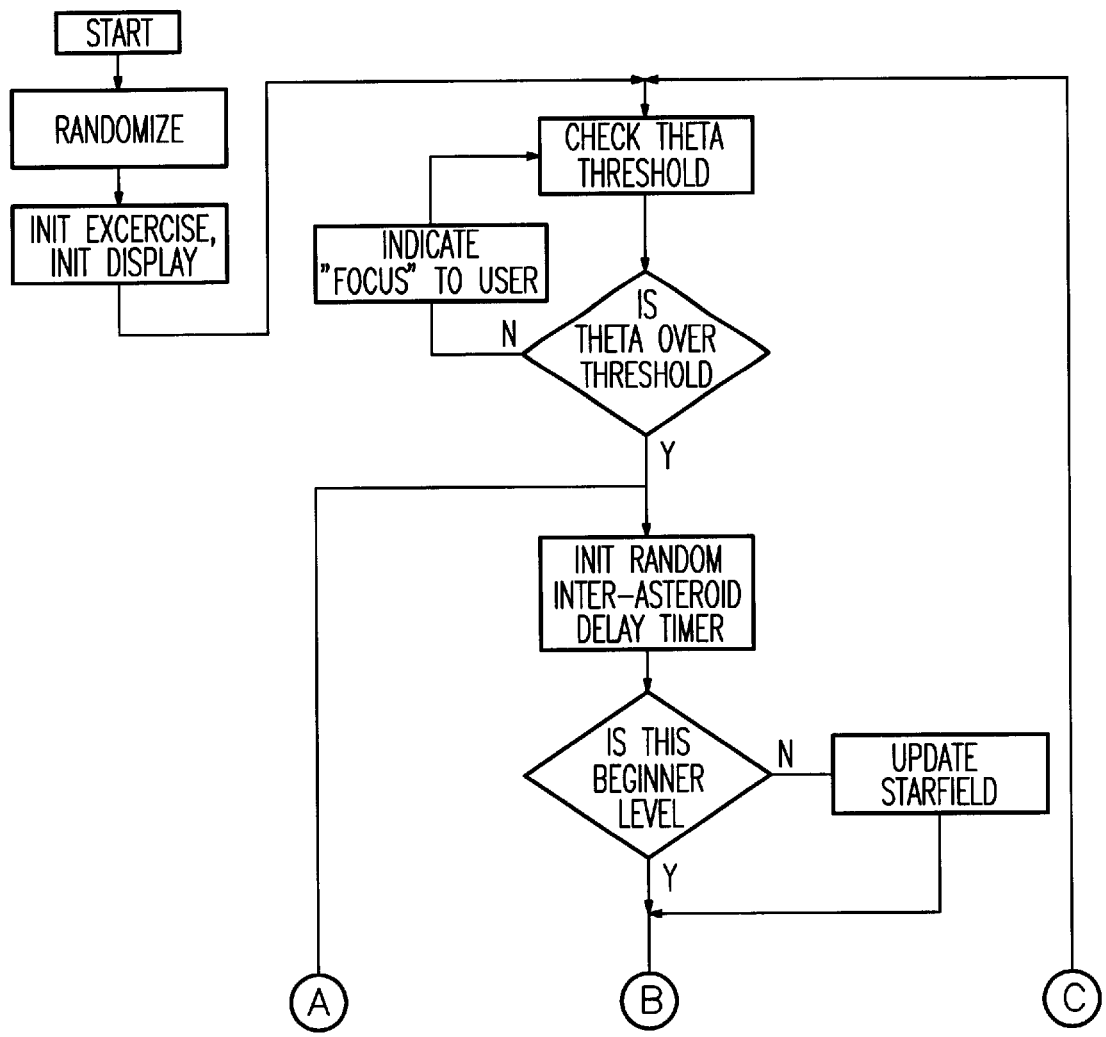
FIGS. 28A and 28B together are an exemplary program flowchart implementing "Starflyer.
Figure 28B:
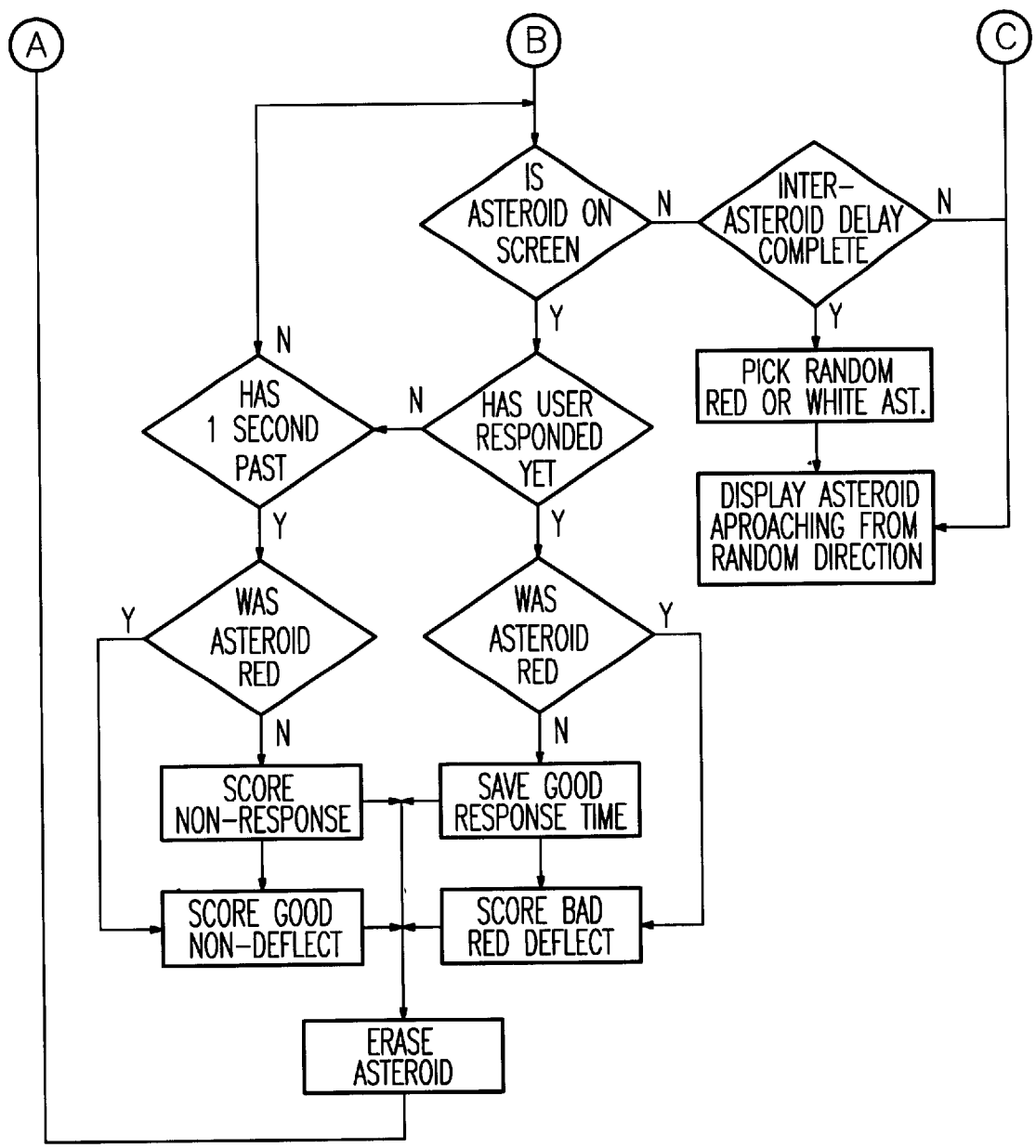

FIG. 27 represents a screen display of an exercise named "Starflyer," and FIGS. 28A and 28B together are a corresponding exemplary program flowchart.

Educational Objective: Mastery of attention while processing and categorizing visual data (visual discriminatory processing).

Goal: The user maintains optimum attention while processing incoming data and inputting responses to the computer.

Procedure: The user plays the game Starflyer to assist in attaining and maintaining an optimum attentive state. During the state of optimum attention, the user views asteroids hurtling towards a cyber cockpit at random speeds and intervals. The user must press the spacebar as quickly as possible to deflect the asteroids except when the asteroid is red. This process allows the user to process, separate and place data in appropriate areas of the brain while maintaining focus. The user is rewarded with five points for correct responses and a loss of ten points for incorrect responses. Reaction speed, accuracy, and impulsivity (a strike of the space bar at an inappropriate time) are measured by software and stored for analysis of progress in upcoming sessions.

To further challenge the user, the particular stimulus to which the user is prompted to respond (e.g. red or white asteroid) can be varied.

Level VI

Figure 29A:
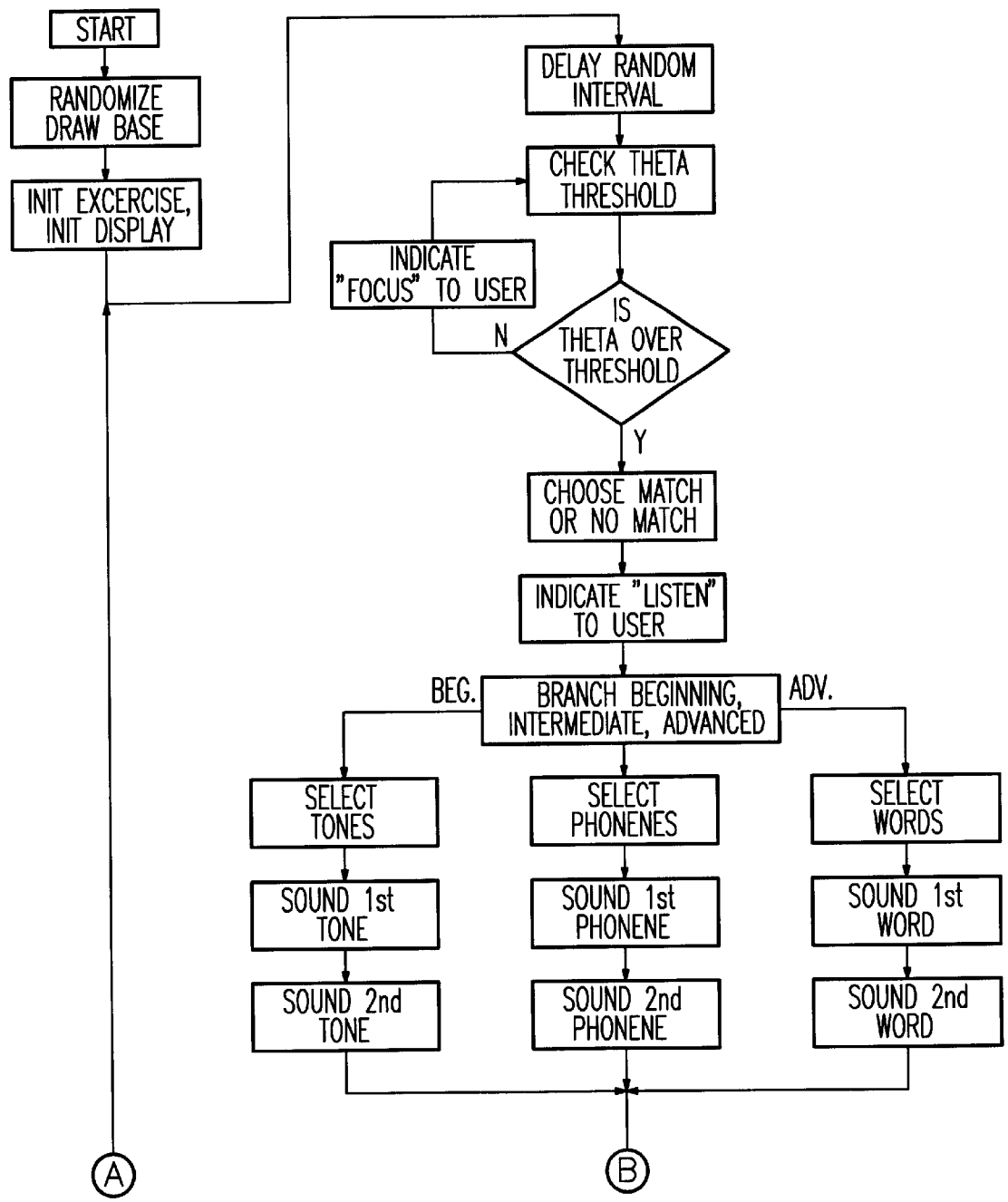
" and FIGS. 29A and 29B together are an exemplary program flowchart of an educational exercise called "Matcher."
Figure 29B:
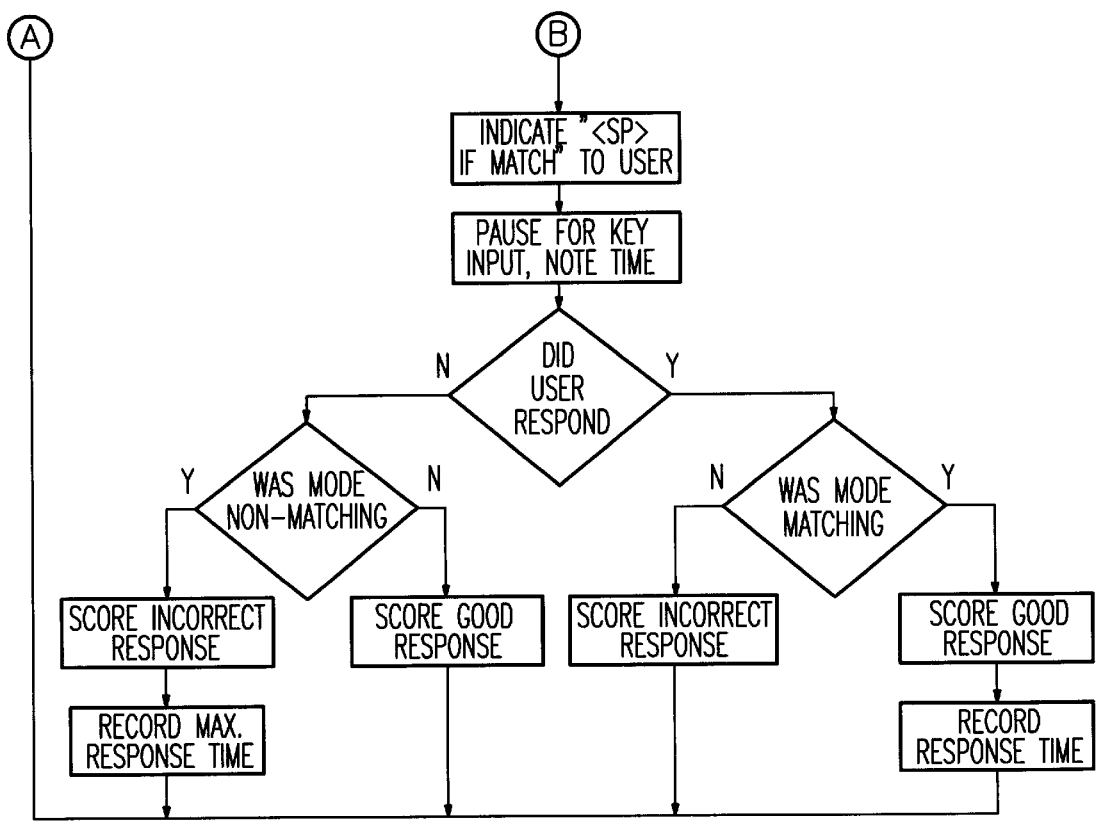

FIG. 29A and 29B together are an exemplary program flowchart of an educational exercise called "Matcher" that employs the computer's sound output capability, as well as the keyboard for user response.

Educational Objective: Mastery of attention while processing and categorizing auditory data (auditory discriminatory processing). Auditory discriminatory processing is the ability to listen to two or more different sounds, phonemes, or words and distinguish the similarities and differences between them.

Goal: The user maintains optimum attention while processing at least incoming auditory data and inputting responses to the computer.

Procedure: Matcher demands that the user maintain focus to begin play and sustain focus to continue play. Detected loss of focus causes the screen to display "Focus to continue," while the words "Focus to continue" can be heard through the computer's sound card and speakers. In the beginner level of Matcher, the user hears two distinct tones emanating from the computer's speaker. If the tones match, the user depresses the space bar. No response is required for a non-match. (Alternatively, response may be required for a non-match, and no response for a match.) The intervals between the pair of tones are delineated by the word "Listen" on the computer screen to distinguish them from a new set. The intervals at which each new set is delivered vary to provide challenge.

In the intermediate level of Matcher, the user hears two distinct phonemes emanating from the computer's speaker. If the phonemes match, the user depresses the space bar. No response is required for a non-match. The intervals between the pair of phonemes are delineated by the word "Listen" on the computer screen to distinguish them from a new set. The intervals at which each new set is delivered will vary to provide challenge.

In the advanced level of Matcher, visual and auditory discriminatory processing are integrated. The user may hear a particular word randomly selected by the computer. If the screen displays the same word as was audibly heard, or a corresponding symbol such as a circle or rectangle, the user processes the space bar. No response is required for a non-match. The intervals between the pairs of words and visual cues are delineated by the word "Listen" on the computer screen to distinguish them for a new set. The intervals at which each new set is delivered vary to provide challenge.

The computer calculates and records the correct responses, incorrect responses, reaction time, time on-task (cumulative time theta signal is above baseline threshold), and impulsive responses (a strike of the space bar at an inappropriate time) to demonstrate improvement over time.

General Discussion

Thus, the apparatus may embody, or be used in conjunction with, a protocol, such as an educational protocol or a training protocol, which incorporates hierarchical mastery of skills, including visual discrimination, auditory discrimination, and/or increased sensory perception.

In one embodiment, a method which incorporates a pedagogy comprises a series of steps or phases of training which progressively build skills that increase the ability of the user to retain and attend to stimuli while disregarding and/or ignoring irrelevant or distracting information. Each phase preferably helps the user to build upon progress in improving concentration that was attained in previous phases.

A particular embodiment comprises a method including six phases.

Phase 1 teaches the user to learn how to pay optimum attention with the aid of a coach. Coaching provides the user with encouragement and reinforcement, especially when the user experiences an inability to pay attention. A user may be rewarded for appropriate levels of attention, for example through the use of visual cues, scoring and/or auditory tones. Thus, initial user training which is directed to increasing attention and thus increasing the capacity for processing information may be achieved by the present invention.

Phase 2 encourages the user to operate a device, particularly a device controlled by circuit logic or program logic or software and more particularly, an educational exercise in the guise of a video game, and thus lengthens the attentive state, without the need of a coach. Changes in one or more measured states, preferably corresponding to a measure of the attentive state in the user, most preferably EEG signals, cause changes in the output or progress or outcome of at least part of a game in which the user plays. Thus, Phase 2 preferably builds upon Phase 1 by allowing the user to experience game changes when optimum attention is paid for extended periods. For example, the user may begin playing with one video game or one phase of the game, whereafter the user is allowed to proceed to the next game or next phase of the game when optimum attention is paid for a five to seven minute period without the use of coaching. Thus, the user is taught and rewarded to extend the attentive state. Furthermore, according to at least one theory of information processing, such encouragement of the attentive state is of importance in, and increases the capacity of, the ability to transfer information (stimulus) into the sensory memory.

Phase 3 further reinforces the attentive state, thereby strengthening the ability of the user to process information (stimulus) into the sensory memory. Preferably, the user begins by optimizing the attentive state as learned in Phases 1 and 2. For example, the user may effect changes in screen color by achieving a maximum attention level as compared to previously attained by a critical base line. Once the maximum attentive state is achieved, the user may view one or more visual forms which represent wholes and parts of identifiable figures. For example, geometric figures may appear on the left side of the screen, while the right side of the screen may depict a portion of the geometric figure which is shown on the left side of the screen. The user must discern, as quickly as possible, if the figures are somehow related. The user will also perform the same task with partial figures of known animals or objects, wherein the user discriminates the completed animal or object from a list on the right side of the screen which may contain an image of the whole animal or object or a portion thereof. The tasks thus teach the user to quickly discern or discriminate the presence of objects and parts while maintaining optimum attention. Preferably, Phase 3 prepares the user or learner to proceed to Phase 4.

Phase 4 teaches the user to maintain optimum attention (for example, by feedback provided by screen color cues) while performing a discriminatory search, such as a visual search of images which exercises the processing of information into the STM. For example, geometric designs may be viewed on the left side of a split screen. The designs may be surrounded by distracting stimuli. One object in this phase is for the user to determine the category of the design or figure as quickly as possible. In another embodiment, a similar test may be presented by auditory tones. This phase of training teaches the user to pay maximum attention while disregarding unnecessary stimuli. Thus, in a progressive sequence of phases of training, the user will have learned to pay optimum attention without coaching, to discern that which is appropriate stimuli, and to disregard irrelevant stimuli.

Phase 5 preferably reinforces Phase 4, and further prepares the user for Phase 6, by teaching the user to pay optimum attention while being monitored by a continuous performance test. The test requires the user to play one or more video games at optimum attention levels. For example, during this session, target images are displayed in a manner as to appear in the path of a flying object. One object is for the user to quickly fire upon the object unless the object is a pre-directed non-target. The rapidity or pace of the games forces the user to selectively discriminate between appropriate data/stimuli and inappropriate data/stimuli. A control means or software preferably monitors the reaction speed, accuracy of hits and misses, and impulsivity of the user. This particular phase teaches the user to not only discriminate between distracting data and relevant data, but to be encouraged when the user is significantly engaging the areas of the STM and working memory which are necessary for information to become encoded in the LTM.

Phase 6 effectively combines the previous phases into a single application, so as to be beneficial for improving the encoding of information into the LTM. This phase also closely simulates educational and clerical processes by allowing the user to maintain optimum attention while transposing data from the left split screen to the right split screen, which may be accomplished, for example, by a manual user input such as through a keyboard, mouse, trackball, pedal, etc. For example, data may consist of words, phrases, mathematical equations, and/or geometric shapes. The present invention therefore provides a training environment which encourages the process of transference, i.e. the ability to apply what one learns to a wider variety of situations and circumstances.

In one particular embodiment, the average millivolt theta activity of a user is determined, whereafter theta thresholds for a user are preferably set at 1 to 2 millivolts lower than the user's average millivolt theta activity. Furthermore, beta thresholds may be set at average millivolt beta activity levels. Averages of theta and beta thresholds may be obtained during a 45 second base line without feedback. It has found that the user may thus immediately, or nearly immediately, perceive his or her level of attention during the biofeedback session in which the user receives some indication of the level or change in level of a variable which corresponds to a measure of the attention level of the user. By way of biofeedback, the present invention encourages the decrease of theta wave activity and the increase of beta wave activity, in a particularly preferred embodiment, by providing rewards after the subject achieves 1 to 2 millivolts decrease in theta and 1 to 2 millivolts in beta activity. It has been found through testing that such a reward scheme is optimal in maximizing the attention and/or concentration of the user, and concomitantly, the relaxation of the user.

Feedback presented to the user may take the form of auditory tones and/or visual graphics as typically presented in the form of video games. For example, further token reinforcement may be supplied by on-screen scoring. In one particular embodiment utilizing a video game, the subject can make a fish dive to the bottom of a video ocean as theta thresholds are decreased and beta increased, thus scoring higher points as displayed on the screen. Furthermore, any increase in theta activity causes the fish to go in the opposite direction necessary to score points. When the subject achieves over 25 rewards per minute on a consistent basis, the threshold (either theta or beta) may be made more difficult. Further one or more thresholds may be lowered, thereby decreasing the demands on. the user for achieving measurable success, when the user otherwise fails to achieve the desired brainwave activity, and thus, concentration levels.

The present invention permits immediate and direct feedback on the attentive state wherein a user can actually hear and/or see when optimum attention is being paid to stimuli, and wherein the user is rewarded immediately, or nearly immediately, thereby encouraging the development of longer periods of sustained attention.

In one aspect, the present invention concerns an apparatus for improving the attention of at least one user, the apparatus comprising means for generating and displaying a video animation, means for measuring electrical activity of the brain of the user, and means for altering the generation of the video animation in response to at least one user input, wherein the user input comprises the measured electrical activity.

The means for altering the generation of the video animation may include means for processing the measured electrical activity so as to be employable by the means for generating and displaying the video animation. The means for measuring electrical activity preferably includes at least one electroencephalographic (EEG) instrument. The means for generating and displaying a video animation preferably includes at least one video display terminal.

The means for generating and displaying the video animation may include means for maintaining the video animation while the measured electrical activity is simultaneously being processed.

In another aspect, the present invention concerns a game having means for generating a video animation, means for displaying the video animation, means for detecting at least one measurement of electrical activity of the brain of the user, and means for processing the electrical activity measurement into at least one indicator signal. The video animation generation means alters the video animation in response to the indicator signal.

In one embodiment, the measured electrical activity is the sole user input upon which changes in the video animation are based. The video animation may be altered in response to changes in the indicator signal.

Furthermore, the processing means is capable of storing the electrical activity measurement and comparing the measurement with at least one previously stored measurement. The processing means may also be capable of comparing the electrical activity measurement to a threshold value.

The threshold value may be determined before the user plays the game, e.g. by a previously inserted or previously measured value. On the other hand, the threshold may be determined after electrical activity of the user has been detected. Thus, thresholds, which are particular to an individual or individuals who are currently interacting with the game, may be obtained from measurements corresponding to that user or other users. While the present invention permits setting thresholds obtained in this manner before a "play session" or "training session," i.e. during a calibration session, the present invention further permits setting thresholds "on the fly" i.e. during a play session or training session, without the need to set thresholds in a calibration session.

Thus, according to the present invention, the user can interact immediately with the game without first being subjected to a battery of tasks or tests in order to establish a baseline or a response template which would then serve as a threshold basis. Furthermore, according to the present invention, thresholds may be determined during the course of a play or training session, e.g. a running threshold may established which adaptively or automatically adjusts to the progress of the user. Thus, the processing means is capable of adaptively or automatically changing the threshold value based upon a comparison between the measurement and at least one previous measurement. Preferably, the processing means is capable of establishing a threshold value based upon at least one previous measurement, for comparison with the electrical activity currently being measured. Thus, the threshold value may be established while the user plays the game.

The present invention may be adapted to accommodate one or more users, either simultaneously or sequentially. For example, the electrical activity of the brain of at least two users may be detected and processed into at least two indicator signals.

In still another aspect, the present invention provides a biofeedback device for improving the concentration of at least one user. The biofeedback device includes means for generating a video animation, means for presenting the video animation, means for detecting at least one measurement which is indicative of the level of concentration of the user, and means for processing the measurement into at least one indicator signal. The video animation generation means alters the course of the video animation in response to the indicator signal, whereby the presentation of the video animation serves as feedback to the user corresponding to the level of concentration of the user.

The detecting means detects an EEG response of the user, which is indicative of the level of concentration of the user. The detecting means may detect at least one of beta waves and theta waves. In a particular embodiment, the detecting means detects both beta and theta waves. Thus, the processing means may convert at least one beta wave measurement and at least one theta wave measurement into at least one indicator signal, and the detecting means measures electrical activity of the brain of the user.

The processing means may include means for selectively filtering at least one frequency range of the electrical activity.

In one embodiment, the electrical activity measurement is the sole external factor upon which changes in the video animation are based.

The video animation may be altered in response to changes in the indicator signal, or the video animation may be altered in response to absolute levels of the indicator signal.

The processing means may be capable of storing the measurement and comparing the measurement with at least one previously stored measurement. The processing means is further preferably capable of comparing the measurement to a threshold value.

In one embodiment, the threshold value is not predetermined before the user plays the game. In that embodiment, the threshold value, or values, is determined as the user plays the game, or the threshold value is set during a pre-game threshold setting session. Furthermore, the processing means may be capable of adaptively or automatically changing the threshold value based upon a comparison between the measurement and at least one previous measurement. Thus, the processing means may be capable of establishing a threshold value based upon at least one previous measurement. For example, the threshold value may be established while the user plays the game.

In yet another aspect, the present invention concerns an apparatus which is capable of detecting at least one EEG signal of at least one user. The apparatus includes at least one EEG probe for picking up at least one electrical signal associated with the brain activity of a user, transmission means for converting the electrical signal into at least one infrared signal, and mounting means for maintaining the probe in contact with the head of the user and for mounting the transmission means on the head of the user.

The apparatus may further include an electrical power source, mounted on the mounting means, for energizing the transmission means.

The present invention may further comprise a system which includes such an apparatus, wherein the system further includes an infrared receiving means for receiving the infrared signal from the apparatus and generating at least one EEG signal. In a highly preferred embodiment, the apparatus and the receiving means are untethered.

The system further may include a computer means and means for delivering the EEG signal to the computer means. The computer means would typically include a computer memory encoded with executable instructions representing a computer program. The computer program is capable of causing the computer means to present a video game. Furthermore, the computer program may be capable of processing the EEG signal as an input into the video game.

In one embodiment, the computer program is capable of storing the EEG signal and comparing the EEG signal with at least one previously stored EEG signal. The computer program is further preferably capable of comparing the EEG signal to a threshold value. The computer program may also be capable of establishing a threshold value based upon at least one previous EEG signal. The threshold value may be stored in the computer memory. Thus, the computer program may be capable of adaptively or automatically changing the threshold value based upon a comparison between the EEG signal and at least one previous EEG signal.

In still another aspect, the present invention provides a method for improving the attention of at least one user. The method comprises the steps of: measuring electrical activity in the brain of a user; presenting a video game to the user; and controlling the video game with at least one user input, wherein the user input comprises the analyzed measured electrical activity. The method may further comprise the step of analyzing the measured electrical activity, wherein the user input further comprises the analyzed electrical activity.

In one embodiment, the analyzed electrical activity is the sole user input for controlling the progress of the video game.

The electrical activity may correspond to alpha, beta, or theta waves. For example, beta and theta wave components may be measured in order to gauge the level of attention of a user.

Thus, the step of measuring electrical activity may include measuring electrical activity in the brain of a user using an electroencephalograph (EEG) instrument.

The step of controlling the video game preferably includes maintaining a video animation while the measured electrical activity is simultaneously being analyzed.

In yet another aspect, the present invention comprises a method for improving the attention of at least one user by biofeedback. The method comprising the steps of: measuring electrical activity of the brain of a user; analyzing the measured electrical activity; presenting a video game having at least one game output to the user; inputting the analyzed electrical activity into the video game; and presenting to the user at least one feedback signal corresponding to the analyzed electrical activity, wherein the feedback signal is manifested by changes in the game output of the video game, whereby the user is rewarded by sensing the changes in the game output of the video game, and whereby the game output assists the user in controlling the electrical activity.

The method also include providing active user inputs to the video game, such as those provided by actuation of a keyboard, mouse, trackball, pedal, touch screen, stylus, button, lever, touch pad, or the like.

The electrical activity may be analyzed in a computer means having a processing means and a memory means.

Furthermore, the method may include transmitting the electrical activity to the computer means by infrared signal.

Game output may include a variety of outputs to the user, such as video, audio, tactile, or other sensory reward.

A user may, for example, be rewarded for achieving at least one level of electrical activity, or for maintaining at least one level of electrical activity for a predetermined period of time.

The video game may further presents a plurality of visual images to the user, wherein the user is rewarded for identifying at least one association between at least two of the visual images and for inputting a direct user input corresponding to the association.

Alternately, or in addition, the video game may present at least one primary game output and at least one distracting game output to the user, wherein the user is rewarded for identifying the primary game output and for inputting a direct user input corresponding to the identification.

Accordingly, the present invention EEG based biofeedback system may be incorporated as an integral component of an overall plan to develop learning skills, attention arousal, and metacognitive skills with children and adults through the use of interactive software. The present invention thus may be used to assist the user in becoming aware of, developing and understanding his or her own capabilities in controlling attention and behavior. Thus, in addition to an appropriate learning environment, positive reinforcement, study skills training, counseling, the present invention EEG based biofeedback system enables the user to teach himself or herself to perform to his or her highest potential.

While specific embodiments of the invention have been illustrated and described herein, it is realized that numerous modifications and changes will occur to those skilled in the art. It is therefore to be understood that the appended claims are intended to cover all such modifications and changes that fall within the true spirit and scope of the invention.

What is claimed is:

1. Apparatus for teaching a user to maintain visual tracking of a moving object while maintaining focus and cognitive processing, said apparatus comprising:

a system for measuring electrical activity of the brain of the user to obtain signals having values indicative of levels of focus and cognitive processing, respectively, and comparing the signals to respective reference threshold values to generate an on-task signal when at least threshold levels of focus and cognitive processing are achieved; and a computer device for generating a representation of an object on a display, and causing the object to randomly move while the on-task signal is being generated.

2. The apparatus of claim 1, wherein said computer device generates a representation of a bug on a leaf.

3. The apparatus of claim 1, wherein said computer device generates a representation of a frog on a pad.

4. The apparatus of claim 1, wherein said computer device generates a representation of an object that moves more frequently as the user achieves greater focus.

5. The apparatus of claim 1, which further comprises a recording device; and wherein said computer device measures and saves to said recording device the level of performance of individual users.

6. The apparatus of claim 1, which further comprises a recording device; and wherein said computer device accumulates and saves to said recording device the cumulative time on task of individual users.

7. Apparatus for teaching a user to increase time on task by challenging the user to complete a task within a predetermined length of time by maintaining focus, said apparatus comprising:

a system for measuring electrical activity of the brain of the user to obtain at least one signal having a value indicative of level of focus and comparing the at least one signal to a reference threshold value to generate an on-task signal when at least a threshold level of focus is indicated; and a computer device for generating a representation of a task on a display, and causing a moving representation of forward progress on the task while the on-task signal is generated.

8. The apparatus of claim 7, wherein said computer device causes a representation of reverse progress on the task when the on-task signal is not being generated.

9. The apparatus of claim 7, wherein the task represented is building a structure of discrete elements.

10. The apparatus of claim 7, wherein the task represented is building a tower of blocks.

11. The apparatus of claim 9, wherein said system and computer device function to increase the number of discrete elements required to complete the task after the user successfully completes the task within the predetermined length of time.

12. The apparatus of computer claim 7, wherein said system and computer device function to increase the level of difficulty after the user successfully completes the task within the predetermined length of time.

13. The apparatus of claim 7, wherein said computer device further generates distractions selected from a group consisting of visual distractions on the display and audible distractions to increase the level of difficulty.

14. The apparatus of claim 7, which further comprises a recording device; and wherein said computer device measures and saves to said recording device the performance of individual users.

15. The apparatus of claim 7, which further comprises a recording device; and wherein said computer device measures and saves to said recording device the cumulative time on task of individual users.

16. Apparatus for teaching a user to improve short term memory sequencing while maintaining a heightened level of attention, said apparatus comprising:

a system for measuring electrical activity of the brain of the user to obtain at least one signal having a value indicative of level of attention and comparing the at least one signal to a reference threshold value to generate an on-task signal when at least a threshold level of attention is indicated;

an input device; and a computer device for generating representations of a plurality of objects on a display, each of the object representations having an inactive and an active display state, said device operable, when the on-task signal is generated, to individually activate the display objects in a sequence while promoting the user to watch, to prompt the user to respond on said input device with a remembered sequence, and to indicate success or failure to the user.

17. The apparatus of claim 16, further comprising a sound generator for outputting tones simultaneously with the activation of the display objects.

18. The apparatus of claim 16, wherein:

said input device is a computer keyboard; and wherein said computer device generates representations of four rectangles arranged in the same pattern as cursor arrow keys on said keyboard.

19. The apparatus of claim 16, wherein said computer device functions to increase the length of the sequence after the user has achieved success a predetermined number of times.

20. The apparatus of claim 16, which further comprises a recording device; and wherein said computer device measures and saves to said recording device the level of performance of individual users.

21. The apparatus of claim 16, which further comprises a recording device; and wherein said computer device accumulates and saves to said recording device the cumulative time on task of individual users.

22. Apparatus for teaching a user to improve short term memory sequencing while maintaining a heightened level of attention, said apparatus comprising:

a system for measuring electrical activity of the brain of the user to obtain at least one signal having a value indicative of level of attention and comparing the at least one signal to a reference threshold value to generate an on-task signal when at least a threshold level of attention is indicated;

an input device; and a computer device for, when the on-task signal is generated, presenting available keyboard characters on a display in a sequence while promoting the user to watch, to prompt the user to respond on said input device with a remembered sequence, and to indicate success or failure to the user.

23. The apparatus of claim 22, wherein said computer device presents characters at random locations on said display.

24. The apparatus of claim 22, wherein said computer device functions to increase the length of the sequence after the user has achieved success a predetermined number of times.

25. The apparatus of claim 22, which further comprises a recording device; and wherein said computer device measures and saves to said recording device the level of performance of individual users.

26. The apparatus of claim 22, which further comprises a recording device; and wherein said computer device accumulates and saves to said recording device the cumulative time on task of individual users.

27. Apparatus for teaching a user visual discriminatory processing while maintaining focus, said apparatus comprising:
- a system for measuring electrical activity of the brain of the user to obtain at least one signal having a value indicative of level of focus and comparing the at least one signal to a reference threshold value to generate an on-task signal when at least a threshold level of focus is indicated;
- an input device; and
- a computer device for, while the on-task signal is being generated, randomly presenting on a display device individual ones of at least two possible stimuli one at a time, and requiring the user to respond or not respond via said input device depending on the stimulus.

28. The apparatus of claim 27, wherein the particular stimulus which requires a response and the particular stimulus which does not require a response is varied.

29. The apparatus of claim 27, wherein said computer device presents on said display device stimuli in the form of objects that appear in individual ones of at least two colors, and the user is required to respond to one color but not the other.

30. The apparatus of claim 29, wherein:
- said input device comprises a computer keyboard; and wherein:
- said computer device presents on said display device an image of a spaceship cockpit and wherein the objects that appear are representations of asteroids that appear one at a time hurtling towards the cockpit at random speeds and intervals, and the user is required to respond via a key on said keyboard to asteroids of at least one particular color, but not the asteroids of another color.

31. The apparatus of claim 27, wherein said computer device further generates distractions selected from a group consisting of visual distractions on the display and audible distractions to increase the level of difficulty.

32. The apparatus of claim 27, which further comprises a recording device; and wherein said computer device measures and saves to said recording device the reaction time of individual users.

33. The apparatus of claim 27, which further comprises a recording device; and wherein said computer device measures and saves to said recording device the accuracy of individual users.

34. The apparatus of claim 27, which further comprises a recording device; and wherein said computer device measures and saves to said recording device the number of impulsive responses of individual users.

35. The apparatus of claim 27, which further comprises a recording device; and wherein said computer device accumulates and records to said recording device the cumulative time on task of individual users.

36. Apparatus for teaching a user auditory discriminatory processing while maintaining focus, said apparatus comprising:
- a system for measuring electrical activity of the brain of the user to obtain at least one signal having a value indicative of level of focus and comparing the at least one signal to a reference threshold value to generate an on-task signal when at least a threshold level of focus is indicated;
- an input device; and
- a computer device for, while the on-task signal is being generated, randomly generating on a sound output device sequences of two sounds that may or may not match in any particular sequence and accordingly representing two possible cases, and requiring the user to respond in one of the cases and not the other.

37. The apparatus of claim 36, wherein said computer device generates on said sound output device sequences of two tones that may or may not match in any particular sequence.

38. The apparatus of claim 36, wherein said computer device generates on said sound output device sequences of two phonemes that may or may not match in any particular sequence.

39. The apparatus of claim 36, wherein said computer device further generates distractions selected from the group consisting of visual distractions on the display and audible distractions to increase the level of difficulty.

40. The apparatus of claim 36, which further comprises a recording device; and wherein said computer device measures and saves to said recording device the reaction time of individual users.

41. The apparatus of claim 36, which further comprises a recording device; and wherein said computer device measures and saves to said recording device the accuracy of individual users.

42. The apparatus of claim 36, which further comprises a recording device; and wherein said computer device measures and saves to said recording device the number of impulsive responses of individual users.

43. The apparatus of claim 36, which further comprises a recording device; and wherein said computer device accumulates and saves to said recording device the cumulative time on task of individual users.

44. Apparatus for teaching a user visual and auditory discriminatory processing while maintaining focus, said apparatus comprising:
- a system for measuring electrical activity of the brain of the user to obtain at least one signal having a value indicative of level of focus and comparing the at least one signal to a reference threshold value to generate an on-task signal when at least a threshold level of focus is indicated;
- an input device; and
- a computer device for, while the on-task signal is being generated, randomly presenting on a display device and generating on a sound output device particular representations. in visual and auditory form that may or may not match in any particular instance and accordingly representing two possible cases, and requiring the user to respond in one of the cases and not the other.

45. The apparatus of claim 44, wherein said computer device further generates distractions selected from a group consisting of visual distractions on the display and audible distractions to increase the level of difficulty.

46. The apparatus of claim 44, which further comprises a recording device; and wherein said computer device measures and saves to said recording device the reaction time of individual users.

47. The apparatus of claim 44, which further comprises a recording device; and wherein said computer device measures and saves to said recording device the accuracy of individual users.

48. The apparatus of claim 44, which further comprises a recording device; and wherein said computer device measures and saves to said recording device the number of impulsive responses of individual users.

49. The apparatus of claim 44, which further comprises a recording device; and wherein said computer device accumulates and saves to said recording device the cumulative time on task of individual users.

50. Apparatus for teaching a user at least one component skill of learning, said apparatus comprising:
- a system for measuring electrical activity of the brain of the user to obtain at least one signal having a value indicative of at least one parameter selected from the group consisting of level of focus and level of cognitive processing, and comparing the signal to a reference threshold value to generate an on-task signal when at least a threshold level of the at least one parameter is indicated; and
- a computer device for, when the on-task signal is generated; presenting a display to teach a skill selected from the group consisting of visual tracking, increased time on task, short term memory sequencing, visual discriminatory processing, auditory discriminatory processing, and combined visual and auditory discriminatory processing.

51. Apparatus for teaching a user to improve short term memory sequencing while maintaining a heightened level of attention, said apparatus comprising:
- a system for measuring electrical activity of the brain of the user to obtain at least one signal having a value indicative of level of attention and comparing the at least one signal to a reference threshold value to generate an on-task signal when at least a threshold level of attention is indicated;
- an input device; and
- a computer device for, when the on-task signal is generated, presenting a sequence of representations on a display while prompting the user to watch, to prompt the user to respond on said input device with a remembered sequence, and to indicate success or failure to the user.

52. Apparatus for teaching a user discriminatory processing while maintaining focus, said apparatus comprising:
- a system for measuring electrical activity of the brain of the user to obtain at least one signal having a value indicative of level of focus and comparing the at least one signal to a reference threshold value to general an on-task signal when at least a threshold level of focus is indicated;
- an input device; and
- a computer device for, while the on-task signal is being generated, randomly presenting to the user a decision to be made based on predetermined rules and requiring the user to make a decision.

* * * * *